United States Patent
Rao et al.

(10) Patent No.: US 10,328,219 B2
(45) Date of Patent: Jun. 25, 2019

(54) METHODS AND DEVICES WITH LEAK DETECTION

(75) Inventors: Dushyant Rao, Baulkham Hills (AU); Jeffrey Peter Armitstead, North Sydney (AU); Dinesh Ramanan, Telopea (AU)

(73) Assignee: RedMed Pty Ltd (AU)

( * ) Notice: Subject to any disclaimer, the term of this patent is extended or adjusted under 35 U.S.C. 154(b) by 1151 days.

(21) Appl. No.: 13/812,253

(22) PCT Filed: Jul. 28, 2011

(86) PCT No.: PCT/AU2011/000950
§ 371 (c)(1),
(2), (4) Date: Mar. 28, 2013

(87) PCT Pub. No.: WO2012/012835
PCT Pub. Date: Feb. 2, 2012

(65) Prior Publication Data
US 2013/0317765 A1    Nov. 28, 2013

Related U.S. Application Data

(60) Provisional application No. 61/369,247, filed on Jul. 30, 2010.

(51) Int. Cl.
*A61M 16/00* (2006.01)
*G01M 3/04* (2006.01)

(52) U.S. Cl.
CPC ........ *A61M 16/00* (2013.01); *A61M 16/0051* (2013.01); *A61M 16/0069* (2014.02);
(Continued)

(58) Field of Classification Search
CPC .............. A61M 16/00; A61M 16/0051; A61M 16/0069; A61M 2016/0021;
(Continued)

(56) References Cited

U.S. PATENT DOCUMENTS 5,551,419 A * 9/1996 Froehlich .......... A61M 16/0069
                                                                    128/204.23
5,704,345 A    1/1998 Berthon-Jones
(Continued)

FOREIGN PATENT DOCUMENTS

EP        714670 A2    6/1996
EP       0722747 A2    7/1996
(Continued)

OTHER PUBLICATIONS

Mehta, et al., Leak compensation in positive pressure ventilators: a lung model study, ERS Journal, 2001, pp. 259-267.*
(Continued)

*Primary Examiner* — Alexander Satanovsky
*Assistant Examiner* — Lina M Cordero
(74) *Attorney, Agent, or Firm* — Botos Churchill IP Law LLP

(57) ABSTRACT

Automated methods provide leak detection that may be implemented in a respiratory treatment apparatus. In some embodiments, the detection apparatus may automatically determine and score different types of leak events during a treatment session, including, for example, continuous mouth leak events and valve-like mouth leak events. The detection methodologies may be implemented as a data analysis of a specific purpose computer or a detection device that measures a respiratory airflow or a respiratory treatment apparatus that provides a respiratory treatment regime based on the detected leak. In some embodiments, the leak detector may determine and report a leak severity index. Such an index may combine data that quantifies different types of leak events.

51 Claims, 25 Drawing Sheets

(52) U.S. Cl.
CPC ............ *A61M 16/026* (2017.08); *G01M 3/04* (2013.01); *A61M 2016/0021* (2013.01); *A61M 2016/0039* (2013.01); *A61M 2205/15* (2013.01); *A61M 2205/505* (2013.01)

(58) Field of Classification Search
CPC ...... A61M 2016/0039; A61M 2205/15; A61M 2205/505; G01M 3/04
See application file for complete search history.

(56) References Cited

U.S. PATENT DOCUMENTS

| | | | |
|---|---|---|---|
| 6,152,129 A * | 11/2000 | Berthon-Jones | A61M 16/00 128/200.24 |
| 6,425,395 B1 | 7/2002 | Brewer et al. | |
| 6,546,930 B1 * | 4/2003 | Emerson | A61M 16/0051 128/204.18 |
| 6,659,101 B2 | 12/2003 | Berthon-Jones | |
| 6,675,797 B1 | 1/2004 | Berthon-Jones | |
| 6,694,978 B1 * | 2/2004 | Bennarsten | A61M 16/0096 128/203.24 |
| 7,077,132 B2 * | 7/2006 | Berthon-Jones | A61M 16/00 128/204.18 |
| 7,644,713 B2 | 1/2010 | Berthon-Jones | |
| 7,730,886 B2 | 6/2010 | Berthon-Jones | |
| 2002/0053345 A1 * | 5/2002 | Jafari | A61M 16/00 128/204.23 |
| 2004/0255942 A1 * | 12/2004 | Rapoport | A61M 16/024 128/204.18 |
| 2007/0068528 A1 * | 3/2007 | Bohm | A61B 5/085 128/204.23 |
| 2007/0163590 A1 * | 7/2007 | Bassin | A61M 16/00 128/204.23 |
| 2007/0215146 A1 * | 9/2007 | Douglas | A61M 16/00 128/200.24 |
| 2010/0101574 A1 * | 4/2010 | Bassin | A61M 16/0051 128/204.21 |
| 2010/0186741 A1 | 7/2010 | Aylsworth et al. | |
| 2011/0139261 A1 * | 6/2011 | Closet | F02M 25/0809 137/12 |
| 2011/0192400 A9 * | 8/2011 | Burton | A61B 5/04 128/204.23 |

FOREIGN PATENT DOCUMENTS

| | | |
|---|---|---|
| EP | 1277435 B1 | 3/2006 |
| JP | 02120635 A * | 5/1990 |
| JP | 2000516491 A | 12/2000 |
| WO | 9806449 A | 2/1998 |
| WO | 2007140512 A1 | 12/2007 |
| WO | 2008025064 A1 | 3/2008 |

OTHER PUBLICATIONS

Meyer, et al., Air Leaking Through the Mouth During Nocturnal Nasal Ventilation: Effect on Sleep Quality, 1997, Sleep 20(7): 561-569.*
International Search Report for Application No. PCY/AU2011/000950 dated Jan. 6, 2012.
International Written Opinion for Application No. PCT/AU2011/000950 dated Aug. 27, 2012.
Extended European Search Report for Application No. EP11811648 dated May 2, 2016.
Japanese Office Action issued in corresponding JP application No. 2017-083559 dated Apr. 3, 2018.

* cited by examiner

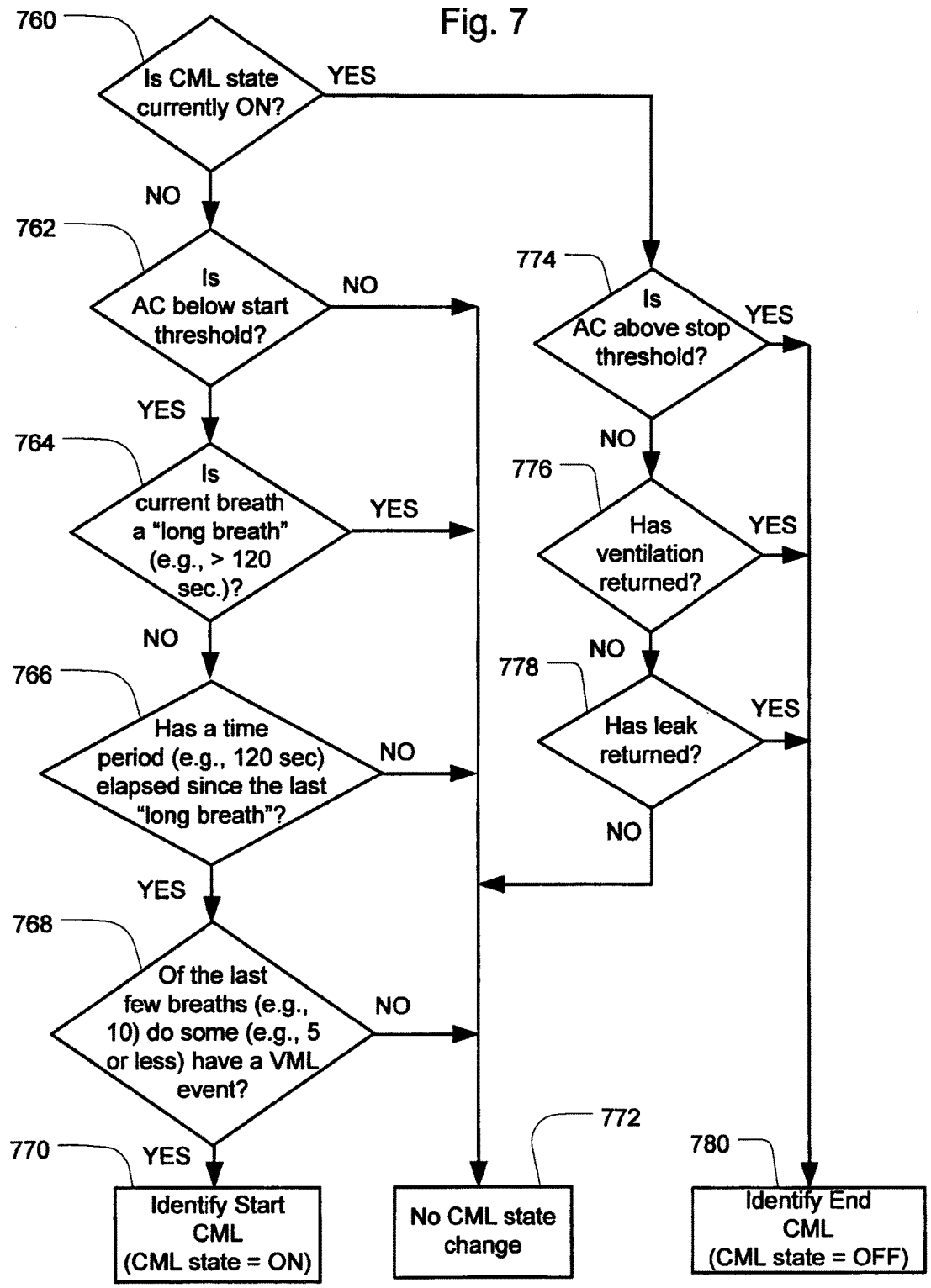

METHODS AND DEVICES WITH LEAK DETECTION

CROSS REFERENCE TO RELATED APPLICATIONS

The present application is a national phase entry under 35 U.S.C. § 371 of International Application No. PCT/AU2011/000950 filed Jul. 28, 2011, published in English, which claims priority from U.S. Provisional Patent Application No. 61/369,247 filed Jul. 30, 2010, all of which is hereby incorporated herein by reference.

FIELD OF THE TECHNOLOGY

The present technology relates to methods and apparatus for detection of leak associated with respiratory treatment apparatus. More particularly, some embodiments of the technology may involve automated leak detection in respiratory treatment apparatus that are enabled for continuous positive airway pressure therapy.

BACKGROUND OF THE TECHNOLOGY

Patients with Obstructive Sleep Apnea (OSA) have recurrent apnoeas or hypopnoeas during sleep that are only terminated by the patient arousing. The best form of treatment for patients with OSA is constant positive airway pressure (CPAP) applied by a blower (e.g., compressor) via a connecting hose and mask. The positive pressure prevents collapse of the patient's airway during inspiration, thus preventing recurrent apnoeas or hypopnoeas and their sequelae. Such a respiratory treatment apparatus can function to supply the patient with a supply of clean breathable gas (usually air, with or without supplemental oxygen) at the therapeutic pressure or pressures, at appropriate times during the subject's breathing cycle.

Respiratory treatment apparatus typically include a flow generator, an air filter, a mask or cannula, an air delivery conduit connecting the flow generator to the mask, various sensors and a microprocessor-based controller. The flow generator may include a servo-controlled motor and an impeller. The flow generator may also include a valve capable of discharging air to atmosphere as a means for altering the pressure delivered to the patient as an alternative or in addition to motor speed control. The sensors measure, amongst other things, motor speed, gas volumetric flow rate and outlet pressure, such as with a pressure transducer, flow sensor, such as a pneumotachograph and differential pressure transducer, or the like. The apparatus may optionally include a humidifier and/or heater elements in the path of the air delivery circuit. The controller may include data storage capacity with or without integrated data retrieval/transfer and display functions.

During respiratory treatment with such a device, it is often useful to measure the subject's respiratory airflow, which may be determined with the flow sensor. However, leak between the mask and the patient are typical. Thus, the flow sensor may measure the sum of the respiratory airflow plus the flow through the leak. If the instantaneous flow through the leak is known, the respiratory airflow can be calculated by subtracting the flow through the leak from the flow at the pneumotachograph.

Known methods to correct for the flow given the leak may assume (i) that the leak is substantially constant, and (ii) that over a sufficiently long time, inspiratory and expiratory respiratory airflow will cancel. If these assumptions are met, the average flow through the flow sensor over a sufficiently long period will equal the magnitude of the leak, and the true respiratory airflow may then be calculated as described.

It is known to measure leak by calculating conductance of the leak. As described in U.S. Pat. No. 6,659,101, the conductance may be determined by dividing a low pass filtered respiratory airflow measure by a low pass filtered square root of a mask pressure measure. The instantaneous leak may then be determined by multiplying the conductance by the square root of mask pressure.

As described in U.S. Pat. No. 5,704,345 to Berthon-Jones, it is also known to determine an index of the presence of valve-like leak. The index is calculated as the ratio of the peak flow during the first 0.5 seconds of expiration to the mean flow during the second 0.5 seconds of expiration.

Another technology is disclosed in European Publication No. 0 714 670 A2, which includes a calculation of a pressure-dependent leak component. The methodology relies on knowing precisely the occurrence of the start of an inspiratory event and the start of the next inspiratory event. In other words, the leak calculation is formed as an average over a known breath and applied to a subsequent breath.

Mouth leak may still present numerous concerns to respiratory treatment therapy such as nasal CPAP therapy. Such concerns may include the following:

1. A patient's arousal rate and/or apnea and hypopnea index ("AHI") can increase due to leak, impacting the patient's sleep architecture.
2. Ventilatory support might be reduced as a result of nasal inspiratory flow leaking out of the mouth, a particular concern for patients on Bi-level/VPAP therapy.
3. Unidirectional nasal airflow may be established, leading to dehydration of the upper airway, congestion and release of inflammatory mediators. Moreover, unidirectional nasal flow may increase nasal airway resistance, which in turn may increase the propensity for oral flow, resulting in a cycle the creates even more mouth leak
4. Patient compliance may be reduced due to nasal symptoms.
5. Erroneous behavior occurs in patient flow estimates and flow generator control algorithms, since the resulting measured total flow signal may not correctly account for oral flow.
6. Mouth breathing in children has been shown to impact their dentofacial development. Specifically, excessive oral airflow can lead to poor teeth alignment (dental malocclusion), forward head posture, irregular clavicular growth, and increased susceptibility to ear infections.

It may be desirable to develop further methods for detecting and/or measuring leak which may be implemented in respiratory treatment apparatus such as apparatus for detection and/or apparatus for treating upper respiratory conditions such as OSA.

SUMMARY OF THE TECHNOLOGY

A first aspect of some embodiments of the present technology is to provide methods and devices for detecting leak.

Another aspect of some embodiments of the technology is to detect leak in an apparatus that measures a respiratory flow signal of a patient.

A still further aspect of the technology is to implement the detection of leak in a respiratory treatment apparatus, such as a continuous positive airway pressure device.

Some embodiments of the technology involve a method for controlling a processor, such as by a leak detection device, to detect leak such as from a measured flow of breathable gas. In such a method, the processor may determine a plurality of features from a measured flow of breathable gas. The processor may then analyze the plurality of features to determine a leak event based on the plurality of features. The processor may also classify the leak event from a plurality of different types of leak. In some such embodiments, the plurality of different types of leak may include a continuous mouth leak and a valve-like mouth leak.

In some such embodiments, the plurality of features may include a measure of ventilation and/or a measure of instantaneous leak. Moreover, the analysis may involve determination of a contemporaneous change in the measure of ventilation and in the measure of instantaneous leak. The contemporaneous change may be an increase in the measure of instantaneous leak and a decrease in the measure of ventilation. Still further, the analysis may involve a determination of a further contemporaneous change in the measure of ventilation and the measure of instantaneous leak. In such a case, the further contemporaneous change may be an increase in the measure of ventilation and a decrease in the measure of instantaneous leak. Moreover, in some embodiments, the analysis may involve the calculation of a duration of the leak event where the duration begins with the contemporaneous change and ends with the further contemporaneous change.

In some such cases, the plurality of features from the measured flow of breathable gas may include a first value associated with the measure of flow falling a proportion below a maximum flow in a breath and a second value associated with the measure of flow rising above the proportion of the maximum flow in the breath. In such a case, the analysis may involve a determination of a duration value representative of a time between occurrence of the first value and occurrence of the second value. The analysis may also involve a comparison of the duration value to a threshold. In such a case, the analysis may detect that the leak event begins when the duration value falls below the threshold. Similarly, the analysis may detect that the leak event ends when the duration value meets or exceeds the threshold.

Some embodiments of the technology involve a method to control a processor to detect leak, which may be from a measured flow of breathable gas. The method of the processor may involve a determination of a ventilation measure and a leak measure from a measured flow of breathable gas. The processor may then analyze the ventilation measure and the leak measure to detect a contemporaneous change in the ventilation measure and the leak measure. The processor may then identify a leak event based on the contemporaneous change. In some such embodiments, the contemporaneous change may be an increase in the measure of leak and a decrease in the measure of ventilation. Alternatively, the contemporaneous change may be a decrease in the measure of leak and an increase in the measure of ventilation. In such a processor, the analysis of the ventilation measure and the leak measure may detect a further contemporaneous change in the ventilation measure and the leak measure. Optionally, the processor may determine a duration of the leak event such that the duration begins with the contemporaneous change and ends with the further contemporaneous change.

In some such embodiments, the contemporaneous change may be an increase in the measure of leak and a decrease in the measure of ventilation and the further contemporaneous change may be a decrease in the measure of leak and an increase in the measure of ventilation. Optionally, the measure of ventilation may be a low pass filtered absolute value of the measure of flow divided in half, and the measure of leak may be an instantaneous leak determined as a function of a calculated leak conductance.

In some such embodiments, the analysis may include a determination of a covariance with data representative of the ventilation measure and of the leak measure. It may also involve a determination of a gradient with data representative of the leak measure. Optionally, a product of the gradient and the covariance may be integrated. In such a case, the processor may identify the leak event by scoring a continuous mouth leak based on a comparison of the integrated product with a threshold.

Still further embodiments of the technology may involve a method to control a processor of a leak detection device to detect leak, such as from a measured flow of breathable gas. The method of the processor may involve a determination of a first occurrence associated with the measure of flow falling below a threshold in a breath and a second occurrence associated with the measure of flow rising above the threshold in the breath. The processor may then analyze a duration associated with the first and second occurrences. The processor may also identify a leak event based on this analysis.

In some embodiments, the threshold may be a proportion of a maximum or peak flow of the breath. Moreover, the analysis may involve a comparison of the duration to another threshold. Optionally, the proportion may be a fraction in a range of about five to thirty percent such as a fraction of about seventeen percent such as preferably 17.5%. In some cases, the duration may represent a time between the first occurrence and the second occurrence. Still further, the leak event may be identified as beginning when the duration falls below the other threshold and the leak event may be identified as ending when the duration meets or exceeds the other threshold. In some cases, the other threshold may be a value representative of a number of seconds in a range of about 0.05 to 0.4 seconds or about 0.2 seconds such as preferably 0.18 seconds.

One or more of these detection control methodologies may optionally be implemented by a leak detection apparatus. The apparatus may include a detection controller having at least one processor to access data representing a measured flow of breathable gas. Optionally, it may further include a flow sensor and/or flow generator. The controller may then be configured to determine a measured flow of breathable gas with the flow sensor. Moreover, the controller may be further configured to control the flow generator to produce a breathable gas according to a pressure therapy regime based on the detected leak.

A similar leak detection apparatus may represent an embodiment of the present technology. Again, such an apparatus may include a controller having at least one processor to access data representing a measured flow of breathable gas. The controller may be configured to determine a plurality of features from the measured flow of breathable gas. The plurality of features can then be analyzed to determine a leak event based on the plurality of features. The leak event may then be classified. Optionally, the leak event may be determined to be a mouth leak event, such as a continuous mouth leak event, based on comparing the plurality of features with time and magnitude thresholds.

In some cases, the controller may be configured to determine first and second features from the measured flow of breathable gas. It may be further configured to analyze the first feature to detect a change in the first feature existing for a pre-determined period of time. It may be further configured, based on the analysis of the first feature detecting the change for the pre-determined period of time, to compare the second feature to a threshold. Still further the controller may be configured, based on the comparison, to set a leak indicator such that the leak indicator is representative of a continuous mouth leak.

In some embodiments of the apparatus, the first feature may include a modified covariance signal and/or the change in the first feature may be a negative change. Optionally, the second feature may include a covariance sum. In some cases, the leak indicator may be set to represent a continuous mouth leak if the comparison detects that the second feature falls below the threshold. Optionally, the first and second features may be derived from a measure of ventilation and a measure of instantaneous leak. Further embodiments of the apparatus may include a flow sensor and a flow generator configured to produce a breathable gas for a patient at a pressure above atmospheric pressure. In some such cases, the controller may be further configured to determine the measured flow of breathable gas with the flow sensor and to control the flow generator to produce the breathable gas according to a pressure therapy regime. Optionally, the controller may also be configured to control the flow generator to produce the breathable gas according to the pressure therapy regime based on the leak indicator.

Still further embodiments of the present technology may involve a leak detection apparatus with a controller having at least one processor to access data representing a measured flow of breathable gas. The controller may be configured to determine features from the measured flow of breathable gas, to analyze the features and to generate a leak indicator to rule out a valve-like mouth leak such that the leak indicator is representative of a detection of a mouth leak.

In some such cases, at least one of the features may include a modified covariance signal and/or at least one of the features may include a covariance sum. Similarly, at least one of the features may include a signal indicative of a level of valve-like mouth leak. Optionally, the features may be derived from a measure of ventilation and a measure of instantaneous leak. Similar to other embodiments, the apparatus may also include a flow sensor and a flow generator configured to produce a breathable gas for a patient at a pressure above atmospheric pressure. In such cases, the controller may be further configured to determine the measured flow of breathable gas with the flow sensor and to control the flow generator to produce the breathable gas according to a pressure therapy regime. Optionally, the controller may be further configured to control the flow generator to produce the breathable gas according to the pressure therapy regime based on the leak indicator.

Another example embodiment of the present technology involves a respiratory treatment apparatus for leak detection and leak control. The apparatus may include sensors configured to measure pressure and flow attributable to a breathable gas. It may further include a flow generator configured to produce the breathable gas for a patient at a pressure above atmospheric pressure. The apparatus may also include a controller coupled with the sensors and flow generator. The controller may be configured to control the flow generator to produce the breathable gas according to a pressure therapy regime. The controller may further include a leak detection module configured to detect a leak event based on an analysis of the measured flow signal. It may also include a pressure adjustment module configured to adjust a therapeutic pressure supplied by the flow generator as a function of an output of the leak detection module where the adjustment reduces the leak event.

In some such embodiments, the leak detection module may be configured to detect a continuous mouth leak. Optionally, the pressure adjustment module may be configured to decrease pressure as a function of the leak. It may also be configured to increase pressure as a function of the leak. Still further, the pressure adjustment module may be configured to analyze a patient flow signal to calculate an adjustment probability for an increase of pressure and a decrease of pressure. In such a case, the pressure adjustment module may be configured to adjust pressure based on a comparison of the adjustment probability and a threshold.

Additional features of the present respiratory technology will be apparent from a review of the following detailed discussion, drawings and claims.

BRIEF DESCRIPTION OF DRAWINGS

The present technology is illustrated by way of example, and not by way of limitation, in the figures of the accompanying drawings, in which like reference numerals refer to similar elements including:

FIGS. 7 and 7A are flow diagrams of two example embodiments of a method of controlling an apparatus to detect a continuous mouth leak (CML) based on calculation of accumulated covariance;

DETAILED DESCRIPTION

Figure 1:
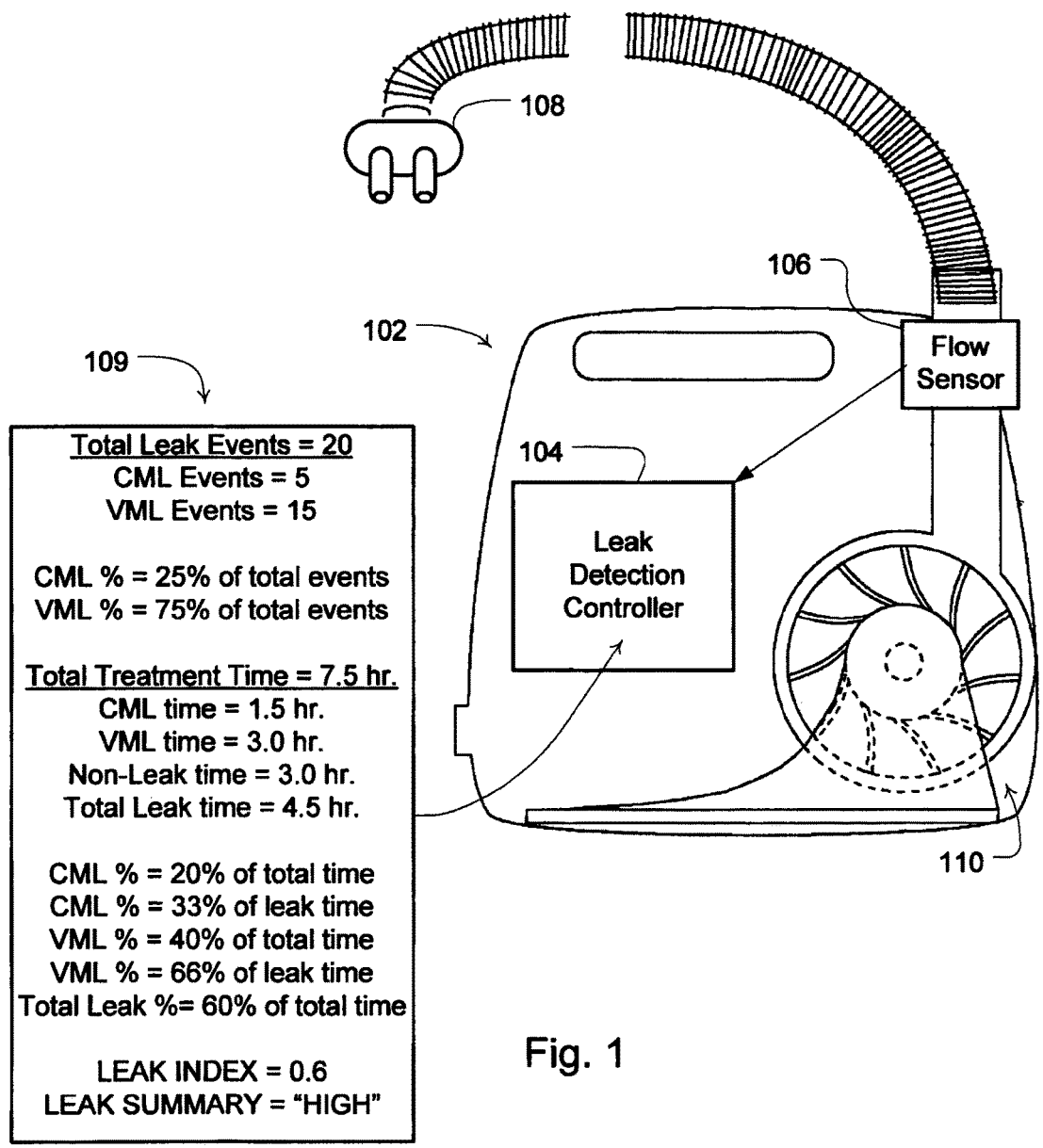
FIG. 1 shows an example leak detection apparatus of the present technology with an optional flow sensor and flow generator.

Accordingly, as illustrated in FIG. 1, embodiments of the present technology may include a leak detection device 102 or apparatus having a controller 104 that may have one or more processors to implement particular leak detection methodologies such as the algorithms described in more detail herein. Thus, the device or apparatus may include integrated chips, a memory and/or other control instruction, data or information storage medium. For example, programmed instructions encompassing such detection methodologies may be coded on integrated chips in the memory of the device or apparatus to form an application specific integrated chip (ASIC). Such instructions may also or alternatively be loaded as software or firmware using an appropriate data storage medium. With such a controller or processor, the device can be used for processing data from a flow signal.

Thus, the processor may control the assessment of leak, such as by detecting leak, differentiating or distinguishing between different types of leak, and/or determining leak times, duration, and severity as described in the embodiments discussed in more detail herein based on measured and recorded respiratory flow data from a prior sleep session. Alternatively, the detection may be performed during a sleep session contemporaneously with the measuring of a respiratory flow signal. Thus, in some embodiments, the device or apparatus itself may optionally be implemented with a flow sensor 106 for measuring a respiratory flow signal for use with the implemented methodologies. For example, flow to or through a nasal cannula 108 or nasal mask or full face mask may be measured using a pneumotachograph and differential pressure transducer or similar device such as one employing a bundle of tubes or ducts to derive a flow signal. Optionally, a flow signal may be inferred from other sensors, such as, a motor current sensor as described in PCT/AU2005/001688 filed on Nov. 2, 2005, the entire disclosure of which is incorporated herein by cross reference.

As further illustrated in FIG. 1, the leak detection device 102 may be implemented to accumulate or generate leak related data such as illustrated leak events data 109 in a leak report that may be stored or output by the leak detection device 102. As discussed in more detail herein, this output may be either visually output on a display of the device or electronically transferred, e.g., wirelessly, to another apparatus. By way of further example, the leak detection device may be implemented with a control methodology to provide a respiratory therapy based on the leak detection methodologies so that the device may serve as a respiratory treatment apparatus. For example, as illustrated in FIG. 1, leak detection device 102 may be optionally implemented with a flow generator 110 such as a servo controlled blower with suitable sensors for such control (e.g., a pressure sensor). Thus, a respiratory treatment or pressure therapy regime, such as a therapeutic pressure level associated with CPAP treatment, may be delivered by the controller of the device. Optionally, the treatment may provide pressure relatively constantly across each breathing cycle of the patient or adjust to provide lower pressure during expiration and higher pressures during inspiration. Therapeutic pressure levels may be automatically adjusted in response to the detection of OSA events (e.g., such as apnea and hypopnea events) that are determined from a leak corrected respiratory airflow signal. Optionally, the detection of leak events or significant quantities of certain leak events may be used to determine if the baseline pressure is deviating. Thus, these measures may be used as a basis or trigger for adjustment to the baseline pressure. Alternatively, a detection of significant leak events may serve to control disabling of automated detection of OSA events or automated changes to treatment pressure levels. Other pressure adjustment schemes may also be implemented. Still further, a detection of significant leak events may serve as a condition of the controller to disable or discontinue the delivery of pressure treatment.

For example, in some embodiments, the detection of leak events, such as the detection of a continuous mouth leak event, may serve as a part of a hypopnea detector. In some automated hypopnea detection devices, a mouth leak may be erroneously scored as a hypopnea event by the automated methodology of the hypopnea detector in the sense of a false positive hypopnea. With the methods described herein, the detection of a leak event contemporaneously with a hypopnea event may be used as a basis to prevent scoring of the detected hypopnea. For example, the scoring of an automatically detected hypopnea event in a breath may be conditioned upon the confirmation of an absence of detected leak events in the breath.

With respect to example detectable leak events, mouth leak may occur in a number of different ways during respiratory treatment therapy, such as nasal CPAP therapy. These leak events may manifest differently in patient flow or a flow signal representative the patient flow from a flow sensor. For example, the leak may be indicative of a continuous mouth leak. Alternatively, it may be indicative of a valve-like mouth leak.

During a continuous mouth leak ("CML"), the patient's mouth remains open continuously, at least in the sense of during essentially most of or the whole of each breath in which the leak occurs. Generally, this leak allows some of the nasally inhaled air to escape from the mouth over the duration of each leak involved breath. Such an event is represented in the signal traces illustrated in the graph of FIG. 2.

Figure 2:
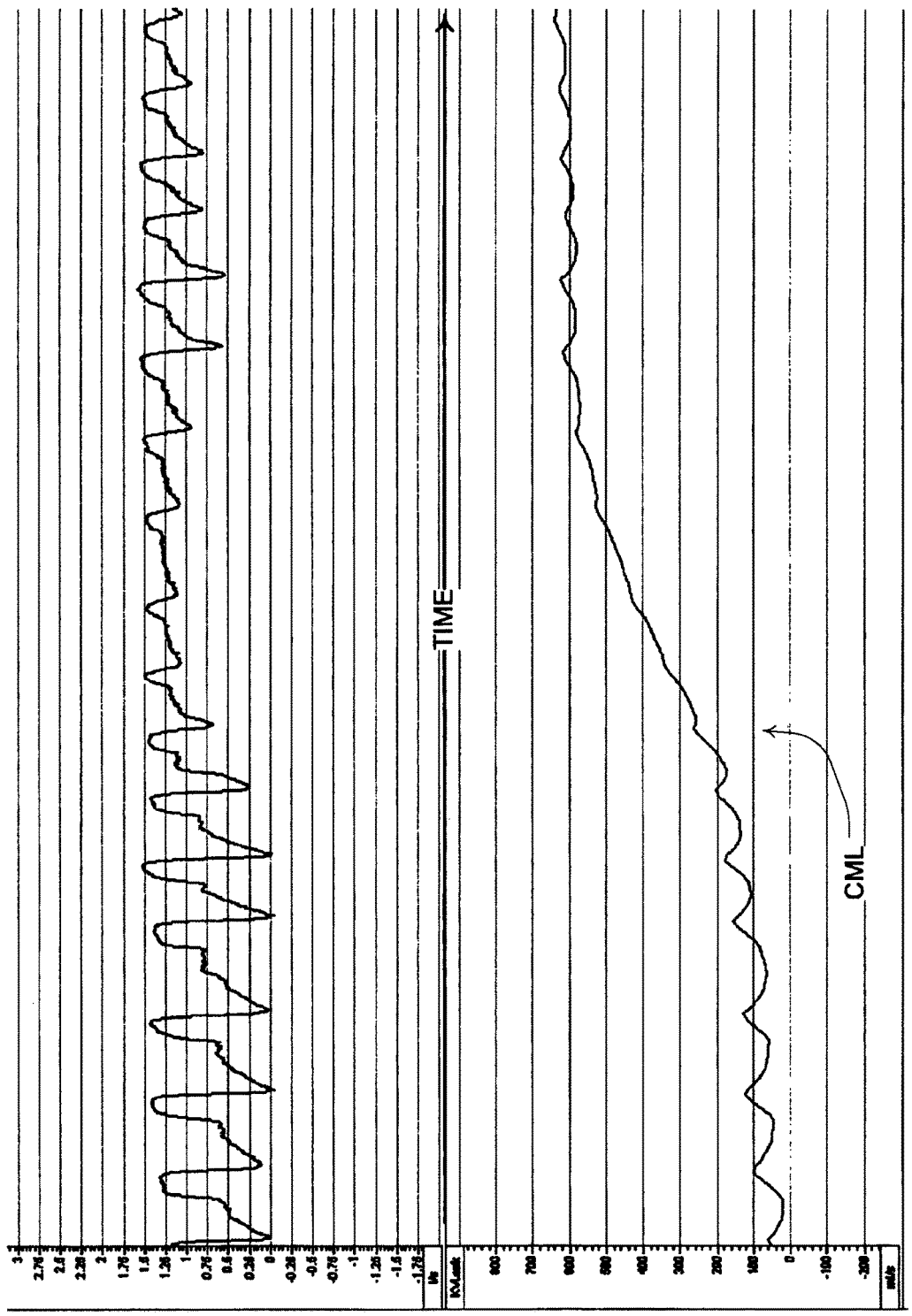
FIG. 2 is a graph that illustrates example flow based features indicative of a continuous mouth leak.

In this regard, FIG. 2 includes an upper graph of a signal trace and a lower graph of a signal trace, both of which are on a common time scale. The upper signal trace shows a measure of flow. The lower trace is a measure of leak, which in this case is an instantaneous leak, such as an instantaneous leak described in U.S. Pat. No. 6,659,101, the entire disclosure of which is incorporated herein by cross reference. The graphs illustrate a time based correspondence between a change (e.g., increase) in the leak measure and a change (e.g., reduction) in ventilation as represented in the flow signal. A detection of such a contemporaneous change may be taken as an indication of the occurrence of a continuous mouth leak or CML in some embodiments of the technology.

During a valve-like mouth leak ("VML"), the air inhaled through the nose is exhaled either partially or completely via the mouth during a portion of a breathing cycle. Generally, the nasal exhalation starts normally, but rapidly falls back up to zero as the mouth "pops" open (like a valve), enabling mouth exhalation. This can manifest as detectable changes in the flow signal such as a sharp negative peak in a nasal flow signal. Examples of such an event are illustrated in the signal trace of the graph of FIG. 3.

Figure 3:
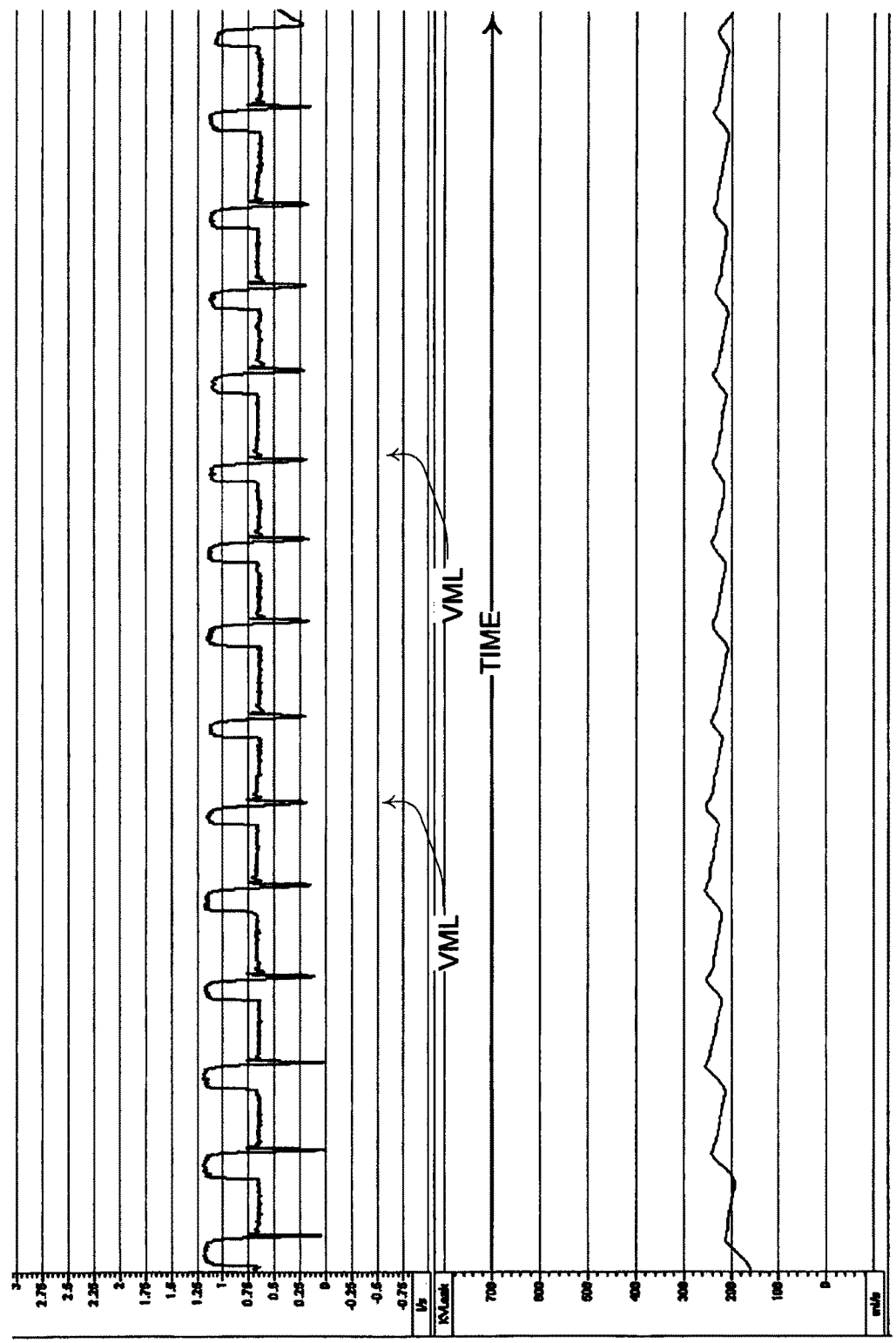
FIG. 3 is a graph that illustrates example flow based features indicative of a valve-like mouth leak.

In this regard, FIG. 3 includes an upper graph of a signal trace and a lower graph of a signal trace on a common time scale. The upper signal trace shows a measure of nasal flow. The lower trace is a measure of instantaneous leak. A detection of such a sharp negative peak in the flow signal may be taken as an indication of the occurrence of a valve-like mouth leak or VML in some embodiments of the technology. As illustrated in lower trace, this detectable change may also correspond with a contemporaneous change in the measure of instantaneous leak.

Thus, as further illustrated in FIG. 1, the leak detection device 102 may detect and report leak events data 109 such as the CML and/or VML events as well as additional data concerning such events. For example, it may distinguish and report a count of such detected events over the course of one or more sleep sessions. The detector may determine the duration of each leak event as well as the time that each event occurs. It may report the session time during which no such leaks occurred. It may further report a break down of the leak events based on their percentage of the total leak events. The detector may further determine a break down of the duration of leak events based on their percentage of a total duration of a sleep session or treatment session or total duration of leak time. The leak detection device 102 may also determine a leak index to summarize a severity of leak. As discussed in more detail herein, this index may combine information for one or more different types of detected leak. The detector may further implement a message warning concerning the leak severity, which may be based on such a severity index.

Figure 4:
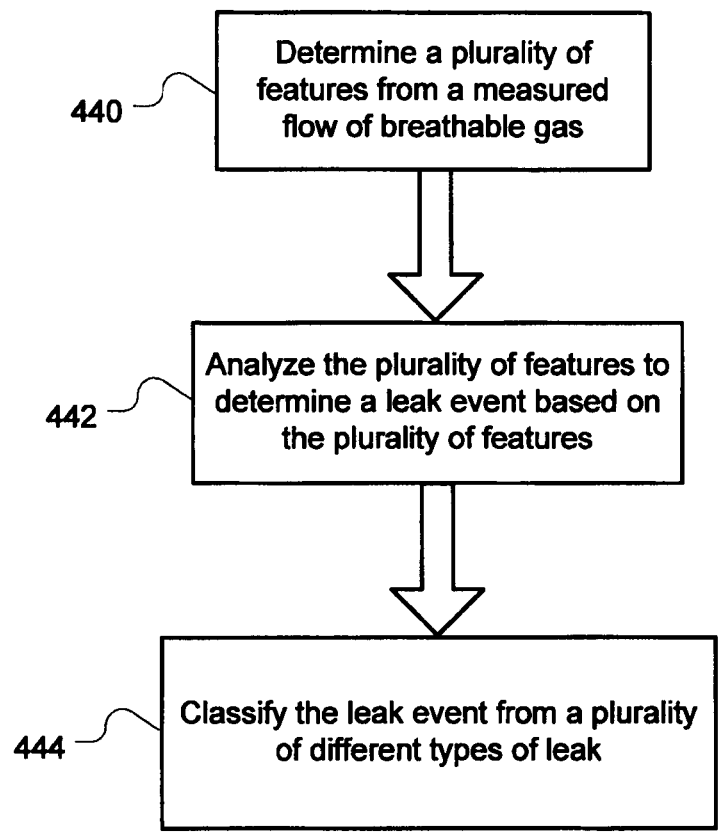
FIG. 4 is a flow chart of an example methodology for an embodiment of a leak detector for distinguishing between different types of leak.

For example, as illustrated in FIG. 4, in some embodiments, the leak detection device 102 may implement a method to control a processor to detect leak from a measured flow of breathable gas. At 440, the method of the processor may involve a determination of a plurality of features from a measured flow of breathable gas. For example, in some embodiments it may detect a measure of ventilation such as a tidal volume. The measure of ventilation may be a minute ventilation (e.g., a measure determined over a period in a range of a half of a minute to five minutes but preferably three minutes). Optionally, such a ventilation measure may be determined by dividing in half the sum of the absolute value of flow samples taken from the flow signal over the period of time (e.g., 0.5 minutes, one minute, three minutes, five minutes). It may also be determined as the integration of half of the absolute value of patient flow (because patient flow considers instantaneous leak and hose drop compensation) over a desired period (e.g., one half, one, three, or five minutes). Still further, it may be determined by low pass filtering of half of the absolute value of patient flow with a time constant of a number of minutes (e.g., one half, one, three or five), but preferably three minutes. Still further, the measure may be a measure of leak or a measure of instantaneous leak as previously mentioned. By way of further example, it may be a peak or maximum flow value of the flow signal or other detectable artefact of the flow signal. At 442, the detector controls an analysis of the plurality of features to determine a leak event based on the plurality of features. The detector may then control a classification of the leak event from a plurality of different types of leak. In this way, the detector may distinguish different types of leak as opposed to simply detecting different leak durations or leak quantities. For example, in some embodiments, the detector may differentiate between CML and VML leak events.

A. Example CML Leak Event Detection Embodiments

Figure 5:
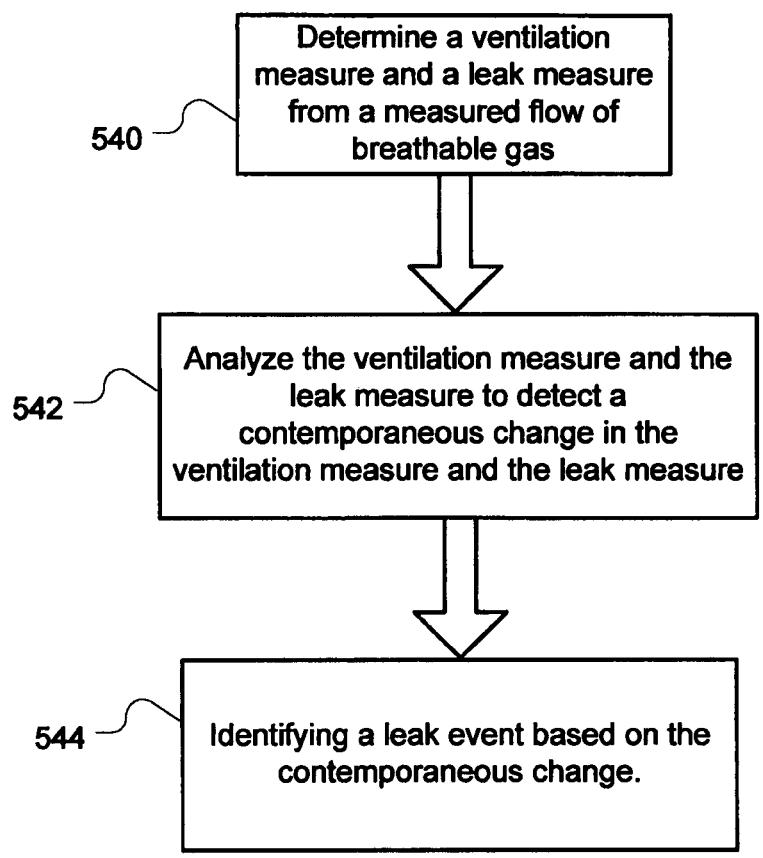
FIG. 5 is a flow diagram of an example embodiment of a method of controlling an apparatus to detect a leak.
Figure 6:
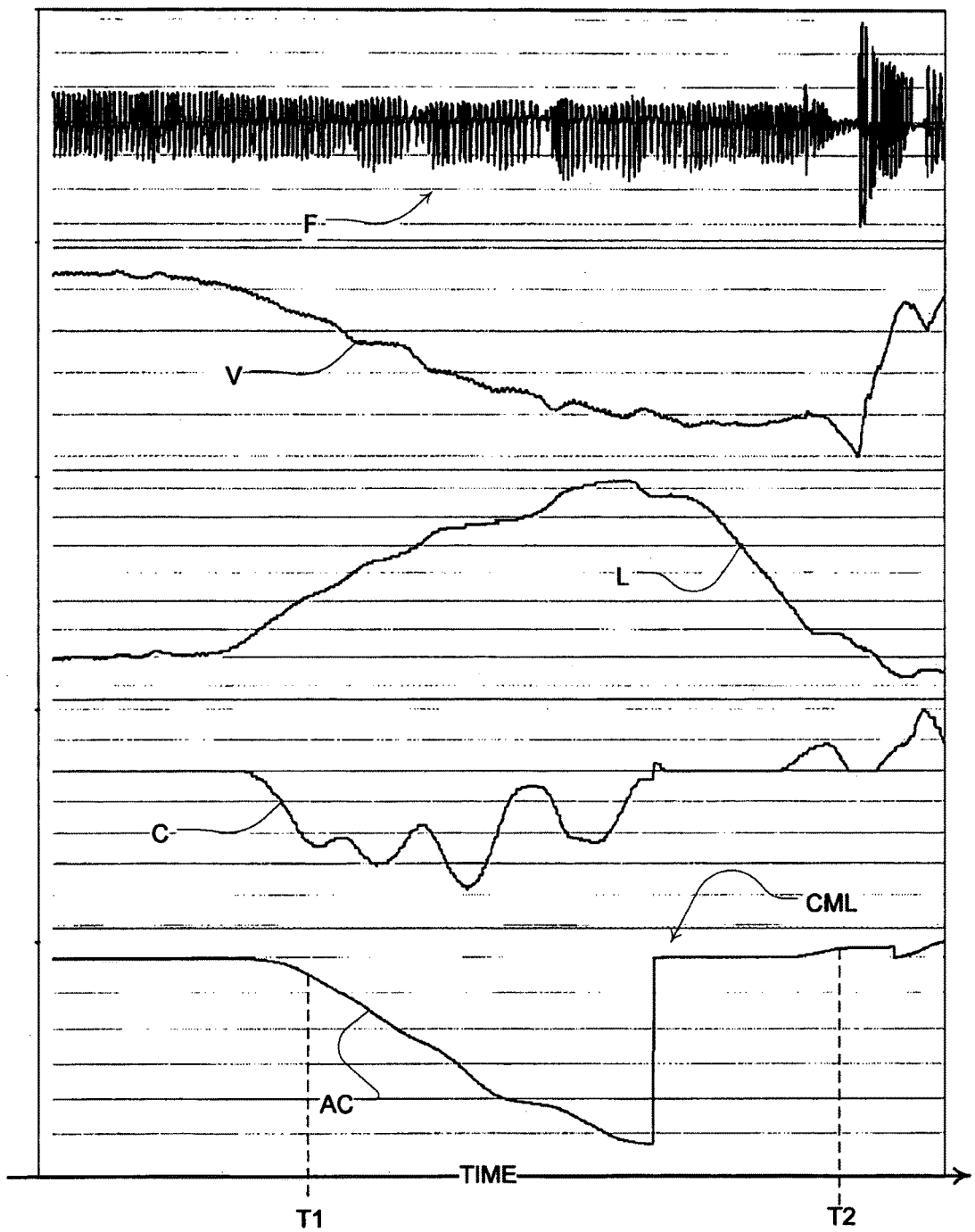
FIG. 6 is a graph of various signal traces relating to a detection of a continuous mouth leak by a leak detector.

Example methodologies that may be implemented for the detection of CML type leak events may be considered in reference to the FIGS. 5 through 7. For example, as illustrated in FIG. 5, in one such embodiment, a processor of a detector may determine a ventilation measure and a leak measure from a measured flow of breathable gas at 540. The processor may then analyze the ventilation measure and the leak measure to detect a contemporaneous change in the ventilation measure and the leak measure at 542. The processor may then identify a leak event based on the contemporaneous change at 544. Such a contemporaneous change may be, for example, a decrease in ventilation with an increase in leak, or an increase in ventilation with a decrease in leak.

Optionally, such a process may be based on a determination of covariance. In such an embodiment, covariance may be determined with the following automated analysis and calculations of a leak detector 102. For such an embodiment, input data may be processed. This input may include sampled ventilation values from a minute ventilation measure (e.g., one minute, three minute, five minute, etc.), sampled instantaneous leak values from a leak measure and sampled patient flow values from a flow signal such as a filtered flow signal. Optionally, this data may be buffered. For example, the flow values may be buffered on a breath by breath basis. Thus, an input module to a leak detector may store current input values (e.g., a ventilation sample and a leak sample and an input vector with flow values that represent a current breath). Such a ventilation process, leak process, breath detection process and covariance process may optionally be conducted as follows:

(1) Ventilation Determination

Flow values may be processed to determine a minute ventilation value (e.g., a three minute ventilation), which may optionally be a smoothed ventilation value. For example, a sample from a flow signal is obtained, which in turn is processed to determine the current smoothed Ventilation value. It also is applied to a patient flow vector as discussed in more detail herein. The ventilation determining process may be as follows:

(a) The Patient Flow value $Q_p$ is obtained.

(b) The smoothed ventilation can then determined with a low pass filter such as an ideal low pass filter. This may be governed by the equation:

$$v_{n_{smoothed}} = a v_n + (1-a) v_{n-1_{smoothed}}$$

where:

$v_n$ is an instantaneous minute ventilation, e.g., given by $$v_n = 60 \times \frac{|Q_p|}{2}.$$

$v_{n-1_{smoothed}}$ is the previous smoothed ventilation value.
$v_{n_{smoothed}}$ is the new smoothed ventilation value.

a may be determined in accordance with a ventilation time constant (τ) (e.g., 30 or 60) and sampling time (Δt) by the following equation:

$$a = \frac{\Delta t}{\tau + \Delta t}$$

Optionally, the ventilation time constant may be in the range of thirty seconds to five minutes. Preferably, it may be about 30 seconds.

The process for determining the smoothed ventilation may be the same as a process for calculating a three minute or five minute ventilation but a different time constant may be implemented.

Optionally, in some embodiments the ventilation measure processing may also be based on arousal detections so as to minimize the affect of breaths associated with arousal in the ventilation measure. If large arousals are allowed to influence the ventilation measure, the ventilation following the arousal will decrease. To avoid such an impact, the ventilation measure may be altered into an "arousal-free" ventilation measure. For example, when an arousal is detected (e.g., based on an "arousal flag" discussed below), the ventilation measure may be held constant or maintained (e.g., by setting the past ventilation value to be the current ventilation value as follows: $v_{n_{smoothed}} = v_{n-1_{smoothed}}$, until normal breathing resumes.

In such a case, an arousal detector may be implemented as follows:

After each breath:
(1) Measure the peak-to-peak flow (e.g., maximum flow minus minimum flow) of the last breath.
(2) If this value is more than some factor (e.g., 1.5 times) greater than the average peak-to-peak flow of the last number of breaths (e.g., last 20 breaths), it is considered an arousal.
(3) When the last breath is an arousal, an "Arousal Flag" is set so that the ventilation measure can disregard values until the flag is reset.

Other arousal detection methodologies may also be implemented.

(2) Leak Determination

Filter an instantaneous leak value, e.g., smooth the input values over time by an ideal low pass filter, which may be governed by the equation:

$$x_{n_{smoothed}} = ax_n + (1-a)x_{n-1_{smoothed}}$$

where:
$X_n$ is the current measured Instantaneous Leak.
$X_{n-1_{smoothed}}$ is the previous smoothed leak value.
$X_{n_{smoothed}}$ is the new smoothed leak value.
a may be determined in accordance with a time constant (τ) (e.g., 20) and sampling time (Δt) by the following equation:

$$a = \frac{\Delta t}{\tau + \Delta t}$$

Optionally, the leak time constant may be in the range of ten seconds to two minutes. Preferably, it may be about 60 seconds.

(3) Breath Buffer

Add the patient flow value to a breath vector or other data structure so as to store the data. This data structure, vector or buffer may be used later for decisions described herein that may implement a breath-by-breath analysis. This buffer may be cleared for each new breath. Thus, the data structure may be used to gather flow data as a function of a detection of each start of inspiration or the end of expiration.

Optionally, these leak and ventilation input values may then be further buffered, e.g., as a circular buffer with smoothed leak values for a chosen time period (e.g., on the order of seconds such as a range of 20-120 seconds, such as about 20 seconds or 30 seconds) and a circular buffer with ventilation values for a chosen time period (e.g., on the order of seconds such as a range of 20-120 seconds, such as about 20 seconds or 30 seconds). Thus, these signal buffers may maintain a record of the latest ventilation values and smoothed leak values, such as the last 20, 30 or 60 seconds of values.

(4) Covariance Determination

A covariance feature C may then be calculated based on the ventilation data and leak data of the circular buffers. Such a covariance feature C may be considered, but need not be identical to, a covariance of two signals. Signal covariance may be considered a measure of how closely two variables increase or decrease together. A high positive covariance indicates that both move strongly together, while a high negative covariance indicates that they move inversely (i.e., while one increases the other decreases).

Thus, the ventilation and leak buffers, which may be denoted $[(v=\{v\})_1, v_2, \ldots, v_n]$ and $[(l=\{l\})_1, l_2, \ldots, l_n]$ respectively may be analyzed by the following process:

(1) First, the covariance (cov) of ventilation and leak may be calculated using the following formula:

$$\text{cov}(v, l) = \overline{(v - \overline{v})(l - \overline{l})} = \frac{1}{n} \sum_{i=1}^{n} \left(v_i - \frac{\sum_i v_i}{n}\right)\left(l_i - \frac{\sum_i l_i}{n}\right)$$

(2) If Cov(v,l)≥0 then the detector may set cov(v,l)=0. This step may be performed if the desire is to focus on a negative covariance (e.g., (1) when the ventilation decreases and leak increases, which may be taken as an indication of a start of a continuous mouth leak event, or (2) when the ventilation increases and leak decreases, which may be taken as an indication of an end of a continuous mouth leak event). Thus, this step can be implemented to disregard a positive covariance.

(3) Optionally, this covariance value may also be multiplied by the sign or signum function of the gradient of the leak buffer. This may permit a differentiation between the start (leak increasing) and finish (leak decreasing) of a leak event. Optionally, to minimize algorithm runtime, the gradient operation may be simplified as an estimate by using only some of the values (e.g., 10 points) evenly spaced along the leak buffer. For example, the gradient may be obtained using:

$$\text{grad}(l) = \sum_{i=1}^{10} [(l_i - \overline{l})(t_i - \overline{t})]$$

where, t={1, 2, . . . , 10}

Thus, in the example embodiment, a final covariance feature value C may be determined with the following formula:

$$C = \text{sign}(\text{grad}(l)) \times \text{cov}(v, l)$$

The covariance feature may then be accumulated over time. For example, the covariance feature C values may be summed or integrated over time to form an accumulated covariance feature AC. For example, the processor may integrate the covariance feature C so as to determine the area under the curve represented by the covariance feature C as it changes over time. This step is desirable for minimizing time dependence. For example, as illustrated in FIG. 6, the covariance feature C may not itself always be large, but may be moderate and maintained over a large period of time. In FIG. 6, signal traces for a flow signal F including a leak event, a ventilation measure V, an instantaneous leak measure L, a covariance feature C and the accumulated covariance feature AC are plotted on a common time axis.

In some embodiments, the accumulated covariance feature AC may be calculated in an automated process as follows:

(1) Start with the feature value of AC=0
(2) For each value of the covariance feature C determined, update the accumulated covariance feature AC with the following formula:

$$AC = AC + t_{slow} \times C$$

Where:

$t_{slow}$ is a multiplier that scales the sum to ensure that a change in sampling time does not change the feature value.

(3) If the last value of C is a different sign or equal to zero, then the accumulated covariance feature AC is reset to zero before adding any new values.

In this way, values of the accumulated covariance feature AC track the magnitude of continuous covariance in one direction (e.g., leak increasing, or leak decreasing).

Optionally, in some embodiments the accumulated covariance signal may be reset (e.g., to zero) based on various additional conditions. Essentially, these are designed to ensure that adverse effects, such as fitting of the mask, pressure adjustment, etc., allow the leak and ventilation values to stabilise before they are relied on in the leak detection processes.

For example, the following conditions may be implemented in some embodiments of the detector:

(a) Over five of the last ten breaths have had a valve-like mouth leak. Such a condition may be taken as an indication that a prolonged VML event has caused the ventilation measure to reduce noticeably, which can occur in severe cases of a VML event. The detector based on the AC signal could report the event incorrectly as a CML event rather than correctly as a VML event. This condition may help to alleviate such a false positive.

(b) When a SmartStart/Stop feature is activated. Smartstart is a feature that allows a respiratory treatment apparatus to automatically start pressure treatment when the apparatus detects a patient breathing from or into a mask. Smartstop allows pressure treatment to automatically stop when the device detects that a patient removes a mask. These detections may be based on detecting certain changes of pressure at the mask. In the event that such features are utilized, the AC signal may be reset to zero when mask removal is detected or when the initial mask use is detected. Such an adjustment of the AC signal may negate large spikes in the leak or ventilation measures that may occur during the initiation of treatment or near the stopping of treatment. This may be detected by evaluating flow data to detect a "long Breath" of over a particular period of time (e.g., two minutes). Optionally, the AC feature may be maintained at zero during an initial period of use time (e.g., a period ranging from one to four minutes, and preferably for about the first two minutes of breathing time.

(c) When Leak Reaches a Particular Level.

When the leak value of the instantaneous leak measure of the leak buffer exceeds a certain threshold (e.g., over 1.5 L/min), the accumulated covariance feature may be reset (e.g., set to zero). Such a significant leak value can adversely affect the detection process and is unlikely to be an indicator of a CML event. In fact, such a high leak is more likely to be an indicator of some fault other than CML.

Accordingly, methodologies for the detection of a CML event may be based on the accumulated covariance feature AC. This may involve one or more comparisons of the AC feature with one or more thresholds. In this regard, the accumulated covariance AC signal trace in FIG. 6 may be taken to indicate that a CML event was initiated at time T1 and stopped at time. T2. The difference of those times may be taken as a measure of duration of the CML event. In the case that T1 and T2 are sample numbers, the duration may be a sample count. Moreover, the magnitude of the accumulated covariance feature AC may serve as a quantifier of the current status of a CML event. Still further, a peak value of the accumulated covariance feature AC in a given CML event, such as a negative peak or a peak of the absolute value of AC, may serve as a measure to quantify a particular CML event. By way of further example, a quantifier of the CML event may be based on the CML event detection and the measure of leak or instantaneous leak. For example, the leak measure during the particular time period of the CML event may serve as a measure of quantity of the CML event. In some embodiments, integrating or summing such a leak measure from the start time of the event to the stop time of the event may serve as such a measure.

In an example embodiment, the accumulated covariance AC may be used as part of an algorithm for CML event detection, such as the detection process of the flow chart of FIG. 7, to determine whether or not there is continuous mouth leak. In such an embodiment, a variable (CML state) may be set to be indicative of whether or not the CML event is occurring based on the accumulated covariance AC feature. This process may cycle for each new value determined for the accumulated covariance AC feature.

In FIG. 7, at 760, the detection process determines the current state of the CML state variable. If the CML state variable is ON (i.e., a CML event is in progress), flow advances to 774. If CML state is OFF (i.e., a CML event is not yet in progress), flow advances to 762.

At 762, the AC feature is compared to a predetermined threshold that may be empirically determined based on known data from one or more patients such as by a machine learning process. For example, if the accumulated covariance AC is below a start threshold (e.g., $-0.19\ l^2/s^2$), process may flow to 764. If it is not, process may flow to 772 where no state change is made to the CML state variable and the process may restart with the next AC value. Optionally, this start threshold may be in a range of about $-0.001\ l^2/s^2$ to about $-2.0\ l^2/s^2$, such as about $-0.133\ l^2/s^2$.

Optionally at 764, the breath vector may be examined to determine whether the current breath is a long breath, such as a breath that exceeds a period of time on the order of minutes or seconds (e.g., a range from about 100 to 140 seconds, but preferably 120 seconds). If the current breath is a "long" breath, process may flow to 772 where no state change is made to the CML state variable and the whole process of FIG. 7 may restart with the next AC value.

Optionally, at 766, a timer may be examined to determine if a period of time has elapsed since the last long breath, which would have allowed for the buffers to get filled and the system to be again fully operable. Optionally, the period of time may be the same or about the same as the period of time that defines a long breath. For example, the period of time may be a range from about 100 to 140 seconds, but preferably 120 seconds). The timer would typically be initiated upon detection of the end of each detected long breath. If the time period has elapsed, flow advances to 768. If the time period has not elapsed, process may flow to 772 where no state change is made to the CML state variable and the whole process of FIG. 7 may restart with the next AC value.

Optionally, at 768, data of prior events is examined to determine if some previous breaths have detected valve-like leak (VML) events. For example, of the immediately preceding few breaths (e.g., a range of five to fifteen but preferably 10), do some of those breaths (e.g., half or less, such as 5) have a VML event. If there is such an event, flow advances to 770 where the CML state variable is set ON to indicate the start or existence of a detected CML event. If there is not, process may flow to 772 where no state change is made to the CML state variable and the whole process of FIG. 7 may restart with the next AC value.

At 774, as a result of a positive response to the query at 760, the accumulated covariance feature AC is compared to another predetermined threshold, which may be the same or different from the start threshold of 762. In this regard, this threshold at 774 may be considered a stop threshold that may be similarly determined by empirical experimentation or analysis. In the example comparison of 774, if the AC feature is not above the stop threshold (e.g., 0.1 $l^2/s^2$), flow advances to 776. If the AC feature is above the stop threshold, process flows to 780 where a state change is made to the CML state variable, setting the variable OFF to indicate the end of the CML event. Optionally, this stop threshold may be in a range of about 0.001 $l^2/s^2$ to about 2.0 $l^2/s^2$, such as about +0.05 $l^2/s^2$. The whole process of FIG. 7 may thereafter restart with the next AC value.

At 776, ventilation is examined to determine if the ventilation measure has or has not returned to its pre-CML detection value. This determination may be based on values of the ventilation buffer and a previously recorded ventilation value that was set at the start of the CML event detection, such as by setting such a ventilation threshold at 770. For example, in 776, if the ventilation has not returned to its quantity at or prior to the start of the current CML event, flow advances to 778. If the ventilation has returned, process flows to 780 where a state change is made to the CML state variable, setting the variable OFF to indicate the end of the CML event. The whole process of FIG. 7 may thereafter restart with the next AC value.

At 778, the detector determines if the measure of leak has returned to its level or quantity prior to the detection of the current CML event. This determination may be based on values of the leak buffer and a previously recorded leak value that was set at the start of the CML event detection, such as by setting such a leak threshold at 770. For example, in 778, if the leak has not returned to its quantity at or prior to the start of the current CML event, flow advances to 772. At 772, no state change is made to the CML state variable and the whole process of FIG. 7 may restart with the next AC value. However, at 778 if the leak has returned, process flows to 780 where a state change is made to the CML state variable, setting the variable OFF to indicate the end of the CML event. The whole process of FIG. 7 may thereafter restart with the next AC value.

With such a process implemented in a processor of a leak detector 102, CML events may be detected. However, in this example embodiment, false negatives are preferred to false positives. To this end, the criteria for detecting the start of a continuous mouth leak CML event are more stringent than the criteria for detecting the end of the CML event.

In the embodiment, as previously mentioned, the testing of the long breath measure may ensure that events such as spikes in ventilation and leak that occur (a) when a treatment device is first started, (b) when the treatment device is started before the mask is placed on the patient's face or (c) due to other extended phenomena, are not falsely classified as CML event.

The testing of leak and/or ventilation measures against a previously recorded starting value at 776 and 778 may ensure that even in adverse situations, the end of the CML event can be detected. For example, in some cases a CML event might continue to hide a leak and there may not be a strong covariance, nevertheless, the described process of the detector may still signify the end of the CML.

In some embodiments, the starting values of leak and ventilation may be recorded based on the process at 770. However, these starting values may also refer to the ventilation and leak values that are coincident in time with the start of a correlation period detected when the sign of the covariance feature C last changes just prior to the detection of the start of the current CML event.

In some embodiments, the threshold comparison of the process in 776 and 778 may involve starting values of the leak and ventilation as well as average values of the ventilation and leak buffers. For example, the starting leak may be compared to an average leak value of the leak values of the leak buffer and the starting ventilation may be compared to an average ventilation value of the ventilation values of the ventilation buffer. For example, if the average of the ventilation buffer is greater than the starting ventilation, the detector may signify that the CML event has ended. Moreover, if the average of the leak buffer is lower than the starting leak, the detector may signify that the CML event has ended.

In some embodiments, as implemented in the process of 768, it may be desirable to check a number of immediately preceding breaths (e.g., a number of breaths in a range of the last 5-15 breaths, such as preferably 10) for valve-like mouth leak events. In severe cases, a prolonged VML event can cause the ventilation to reduce noticeably, which might otherwise be detected as a CML event instead. However, the process of 768 may alleviate this issue.

Figure 7A:
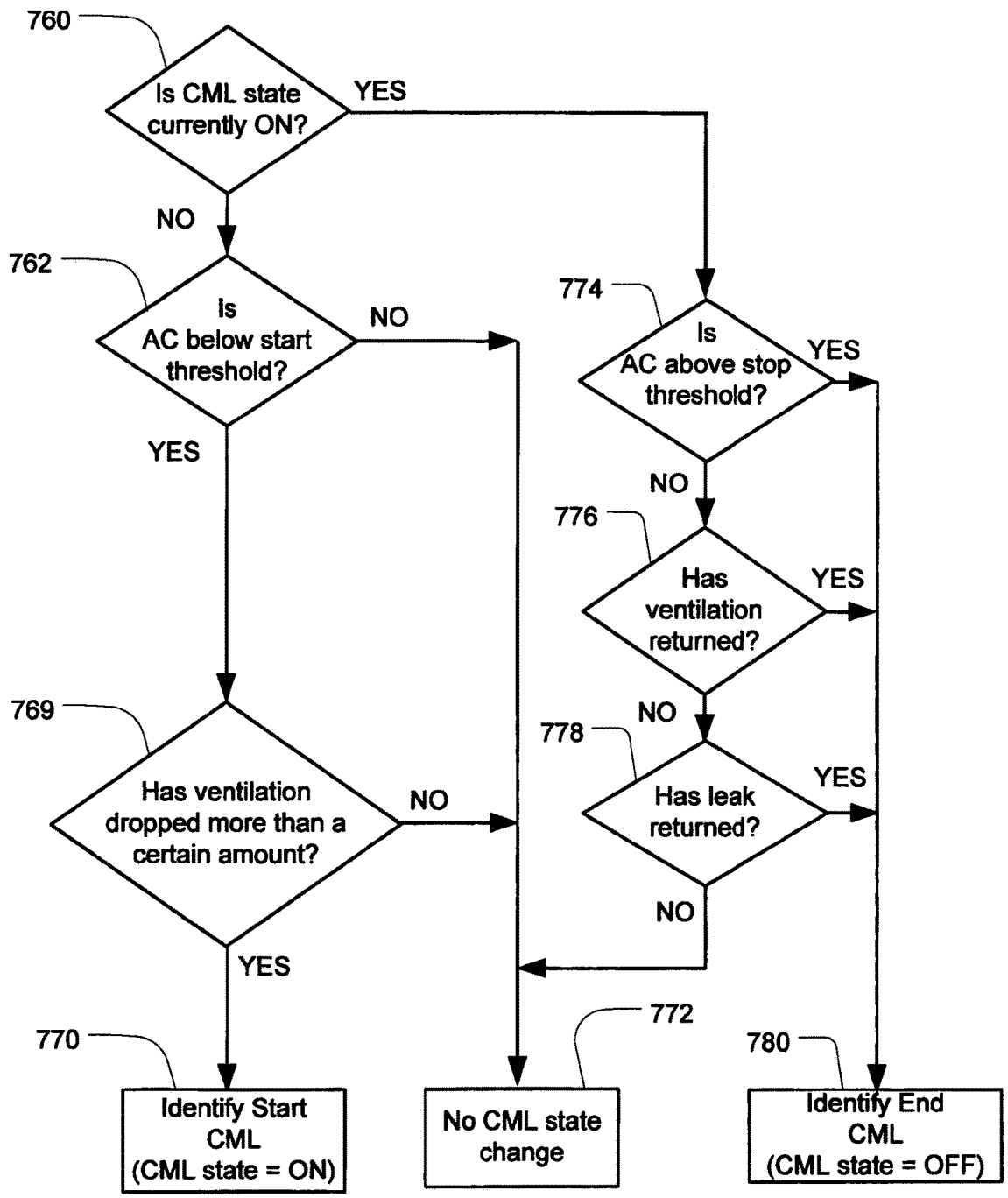

FIG. 7A depicts another example embodiment for detecting a CML based on the accumulated covariance AC. This methodology of this process is comparable to the process of FIG. 7. However, the long breath check at 764, the long breath elapsed check at 766 and the last few breath check of 768 of FIG. 7 are omitted. Moreover, a further optional check at 769 is added in FIG. 7A. At 769, the ventilation measure is checked to determine if it has dropped more than a certain amount, such as, by comparing it to a threshold. The threshold may be associated with a starting ventilation value. Thus, when the start of a potential CML event is detected at 760, the process advances to 769 to determine whether the ventilation has dropped sufficiently such as a drop to less than a fraction (e.g., about 85%) of ventilation prior to the check at 760. In some cases, an enormous mask leak and a miniscule ventilation change may have a strong covariance but would not be the result of an actual continuous mouth leak event. The small ventilation change may be associated with a breathing pattern of the patient. Thus, this check may be implemented to prevent a false positive indication of a CML event if ventilation has not changed sufficiently. Although not shown therein, such a check may also optionally be implemented in the example process of FIG. 7.

Figure 6A:
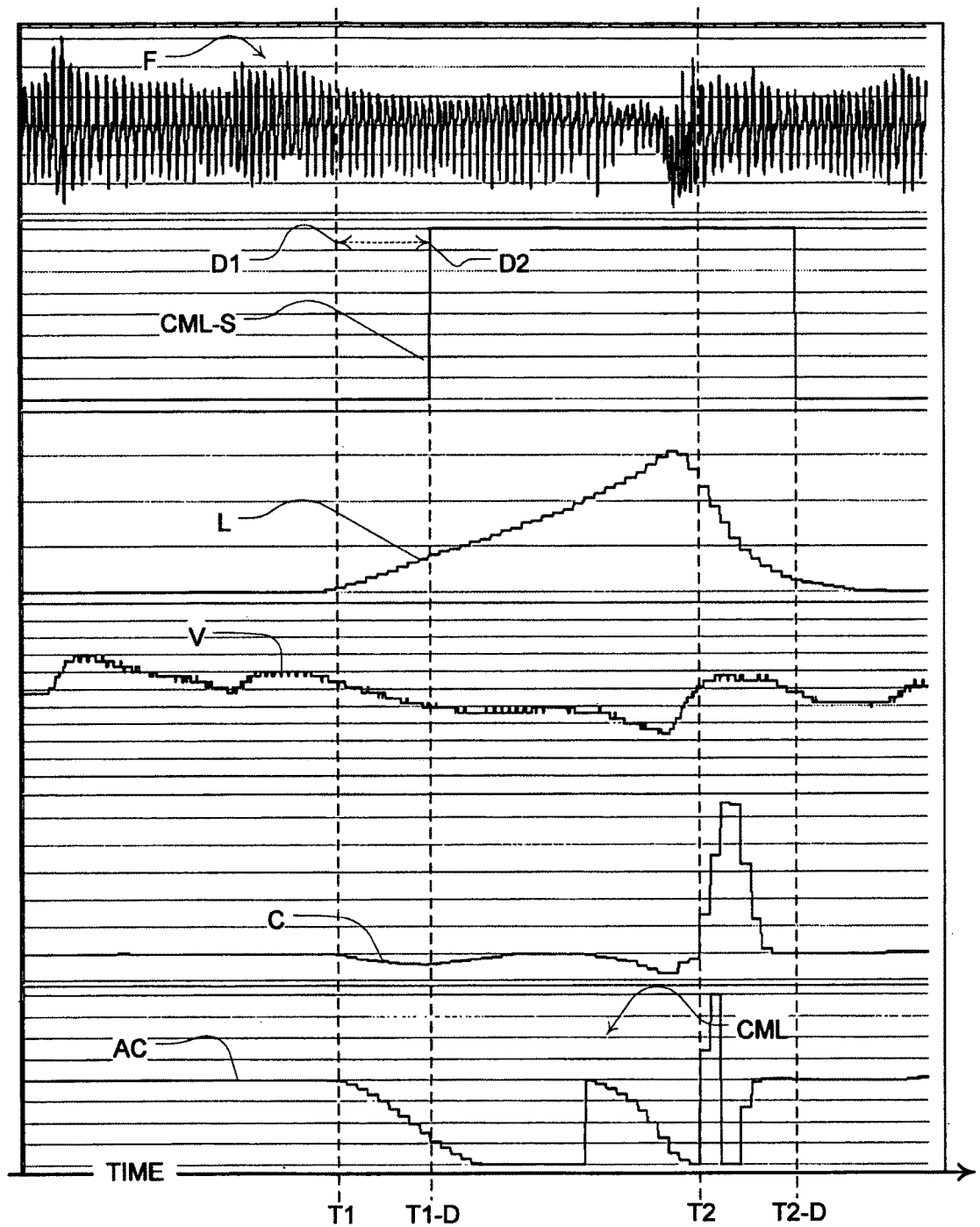
FIG. 6A is a further graph of various signal traces relating to a detection of a continuous mouth leak by a leak detector.

Similar to FIG. 6, a further graph of the signal traces associated with the detection of CML events is shown in FIG. 6A. However, in this version, an additional signal is depicted which may represent the status of the CML state variable (shown in FIG. 6A as CML-S) that may be set by any of the previously described methodologies. The flow signal F, CML state signal CML-S, leak signal L, ventilation signal V, covariance signal C and accumulated covariance signal AC are also plotted on a common time axis. The CML event is illustrated as occurring in the period between time occurrence T1 and time occurrence T2.

As illustrated in FIG. 6A, there may be a delay between the actual time of the onset of a CML event and its detection. Such a delay can be a result of processing the covariance and particularly may be due to the time length of the covariance buffer that may be implemented in some embodiments. To compensate for such a delay, some versions of the detector may implement a covariance time delay (COV_DELAY) that may serve as a further condition for setting the CML state variable to a non-detection state or may be utilized for detecting the time of the CML event. This delay is illustrated in FIG. 6A. In the figure, the delay is illustrated between point D1 (when a CML event actually starts at time occurrence T1) and point D2 (when the detector initially detects the event at time occurrence T1-D). The COV DELAY time is shown as the period of line D1-D2. Thus, in some embodiments, a determination of the time period of the detected event may be adjusted by this delay time associated with the time delay of detection (e.g., T1-D minus T1). For example, this time may be added at the end of the event at T2 to detect a total time of the event. Alternatively, the method for setting the CML state variable off (e.g., process 780 of FIG. 7A) may be conditioned on the running of a timer with an elapsed time period of COV_DELAY before the CML state variable is set to off at time occurrence T2-D) For example, the timer may begin to run upon entering process 780 of FIG. 7A and the CML state variable may be set to OFF when the timer has elapsed the COV DELAY time period.

B. Example VML Leak Event Detection Embodiments

Figure 8:
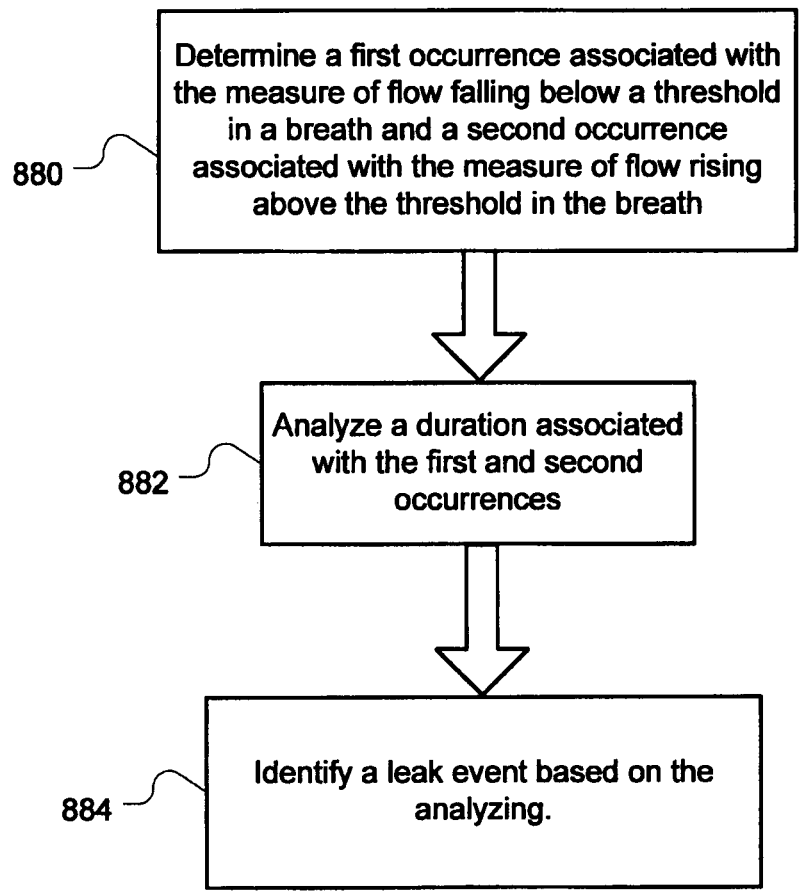
FIG. 8 is a flow chart of a further example methodology for an embodiment of a leak detector.
Figure 9:
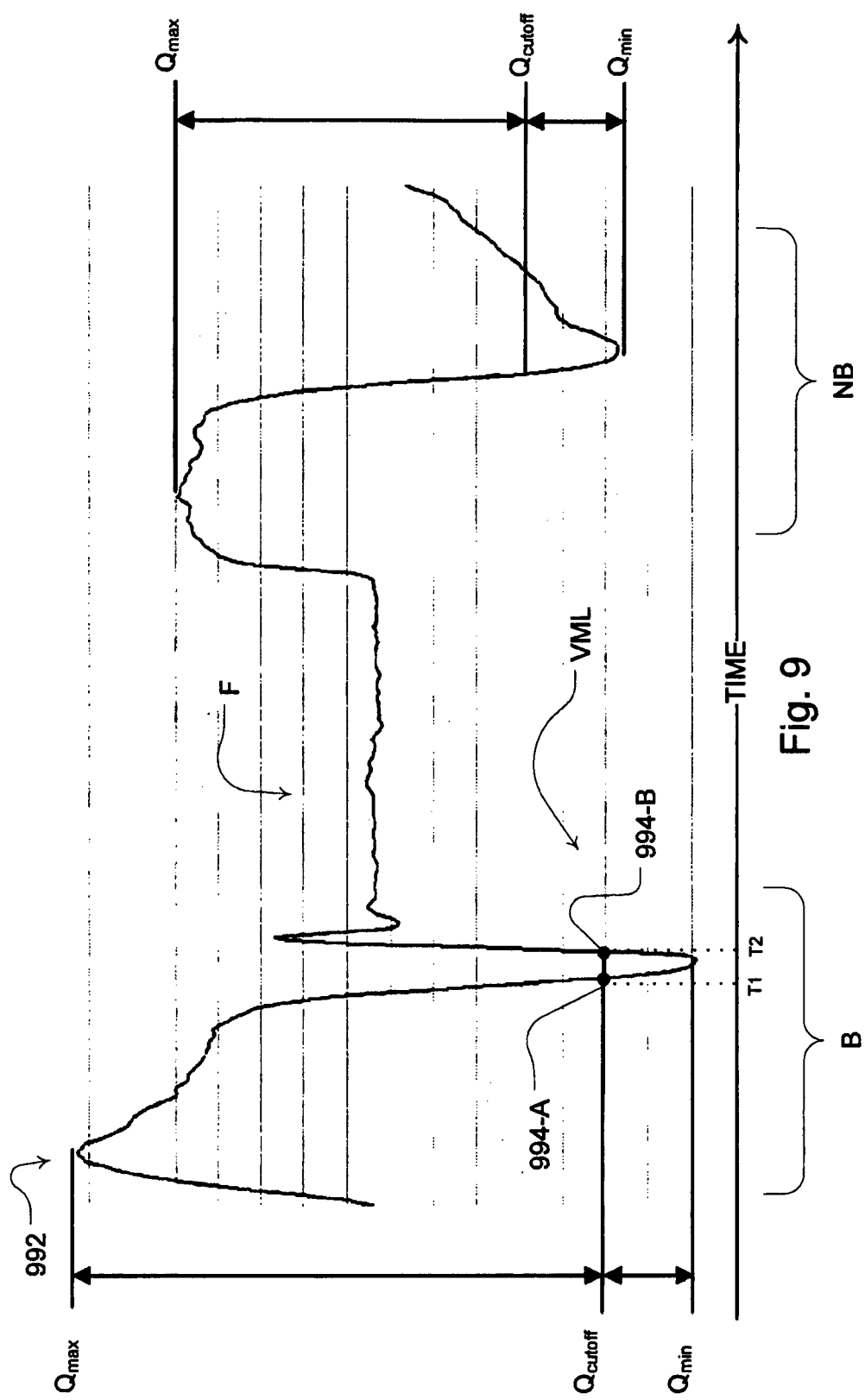
FIG. 9 is a graph of a signal trace of a flow signal illustrating a detection of a valve-like mouth leak by a leak detector.

Example methodologies that may be implemented for the detection of VML type leak events may be considered in reference to FIGS. 8 and 9. In some embodiments, such a process may analyze data from a patient flow signal to detect a sharp negative peak, such as a negative peak during expiration, that may be taken as representing a typical valve-like mouth leak. In one such embodiment, the process may measure the duration (in each breath) over which the patient flow is below a chosen cutoff flow level during expiration. If this duration is considered very short, then it may be considered a sharp negative peak for which it is likely that valve-like mouth leak is occurring.

For example, as illustrated in FIG. 8, in one such embodiment, a processor of a detector may determine a first occurrence associated with the measure of flow falling below a threshold in a breath and a second occurrence associated with the measure of flow rising above the threshold in the breath at 880. The processor may then analyze a duration associated with the first and second flow occurrences at 882. At 884, the processor may then identify a leak event based on the analyzing.

Such a process may be based on the previously described flow buffer that contains data from the flow sensor, and which may be considered data from a filtered flow signal. This data of the buffer may represent a complete breath. Thus, the VML detection process herein may be implemented on a breath-by-breath basis based on data representing a complete breath. An example output from the detection process may then be considered a VML state variable that indicates whether or not the analyzed breath contains a valve-like mouth leak event.

Thus, in this example, the detector processes data from a patient flow signal for a particular breath and determines whether a VML event was present in the breath. Such a process may be considered in view of the flow signal trace of FIG. 9. In the patient flow trace F of FIG. 9, there is a breath B with valve-like mouth leak. In this process, the time spent below a particular flow that is smaller than that of a normal breath NB may be considered in detecting the valve-like leak.

The following calculations may be implemented in an example of this VML detection process:

(1) Determine the value $Q_{cutoff}$ which is at a pre-determined proportion of a predetermined flow that is between the minimum flow $Q_{min}$ and the peak flow 992 or maximum flow $Q_{max}$ for a particular breath. For example, such a proportion may represent a fraction or percentage of the maximum flow $Q_{max}$ for a particular breath. The percentage may be in a range of about 5-30 percent, but preferably about 17%, such as 17.5%.

(2) Determine the occurrence of point 994-A in the breath at which the flow initially falls below $Q_{cutoff}$.

(3) Determine the next occurrence of point 994-B in the same breath at which the flow returns above $Q_{cutoff}$.

(4) Determine the duration (e.g., time or sample count) between points 994-A and 994-B. For example, a time duration may be determined by obtaining times T1 and T2 (shown on the graph of FIG. 9 in association with points 994-A and 994B respectively) and subtracting T1 from T2. Alternatively, an sample count may be utilized as a duration without an actual conversion to a measure of time, such as by counting the number of samples between T1 and T2.

(5) Compare the determined duration to a threshold. For example, if the duration is in seconds, compare the duration to a time threshold, which may be determined empirically with known data of one or more patients, such as by machine learning. For example, a suitable time threshold may be a value in a range of 0.05 to 0.4 seconds, such as 0.14 or 0.18, or about 0.2 s. Alternatively, a duration based on a sample count may be compared to a threshold that represents a pre-determined number of samples.

(6) Set the VML state variable based on the comparison. For example, if the duration is below the threshold, the VML state variable may be set ON to indicate the detection of a VML event in the breath; otherwise, the VML variable may be set to OFF to indicate that no VML event was detected in the breath.

The number and timing of such events may then be scored over a treatment session. Optionally, the determined duration for the particular VML event of a breath may be taken and reported as a measure that quantifies the significance of the particular VML event.

C. Further Example Embodiments

Further examples of the present technology may be considered in view of the embodiment of FIGS. 10 through 17 which may also implement detections of CML and/or VML events.

Figure 10:
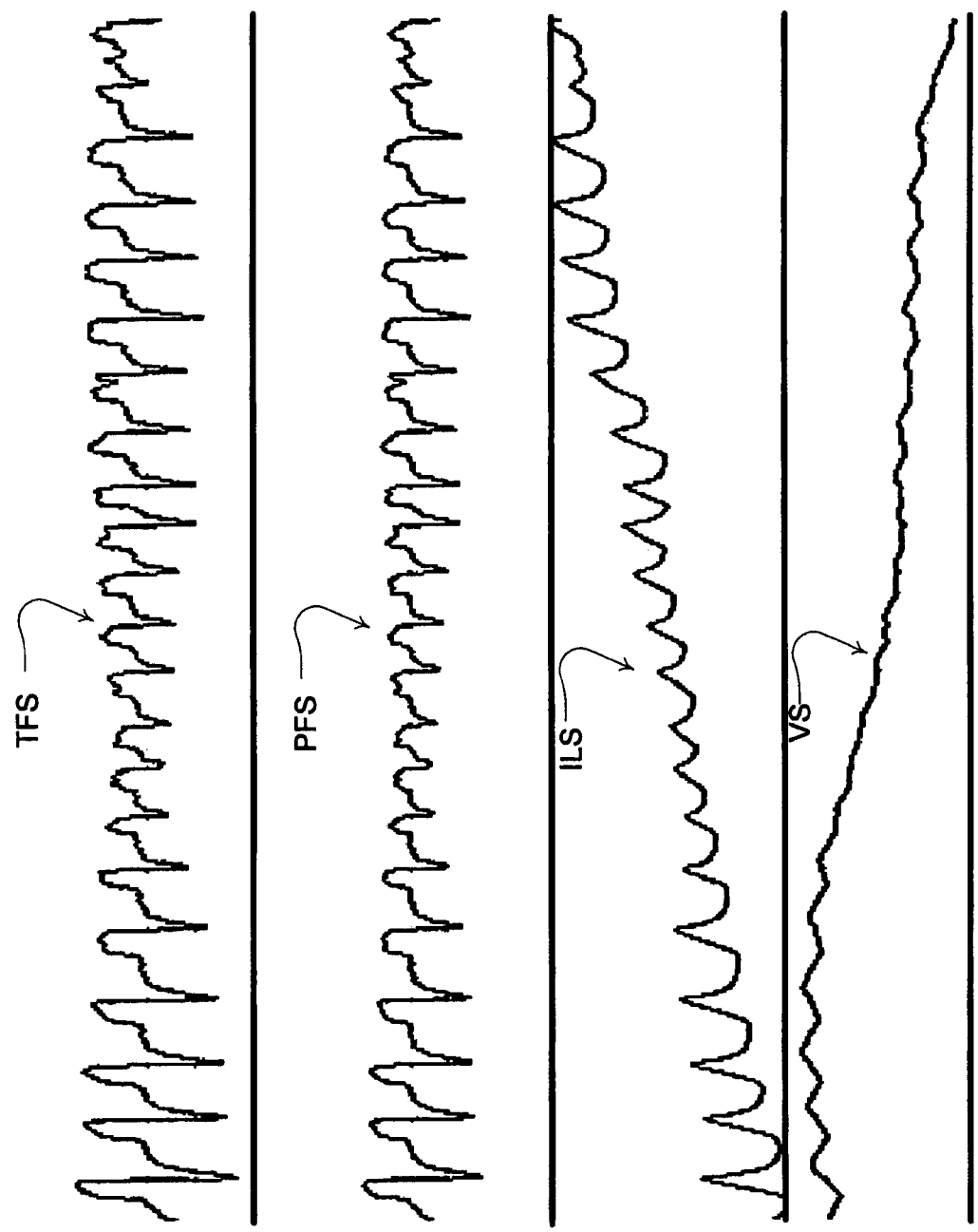
FIG. 10 is a graph that illustrates example flow based features that may be indicative of a continuous mouth leak.

In this embodiment, the determination of a Continuous Mouth Leak, such as by a processing algorithm, may be based on a ventilation signal and a leak signal. In this embodiment, if there is a decrease in ventilation with a simultaneous increase in leak, this signifies the start of CML. Also, an increase in ventilation accompanied by a decrease in leak indicates the end of CML. FIG. 10 illustrates data typical of an epoch captured during a period of CML. Typically, there is a continuous flow of air through the mouth during such periods and the apparent ventilation will reduce and leak detected by the flow generator will increase. FIG. 10 contains signal graphs on a common time scale including a total flow signal (TFS) which is a raw blower flow signal such as from a flow sensor. Also shown is a patient flow signal (PFS) which is a signal derived by subtracting an instantaneous leak signal and a vent flow signal from the total flow signal. Whilst any measure of leak can be used (see U.S. Pat. No. 6,659,101), in this specific embodiment the instantaneous leak signal (ILS) may be a mean mask flow corrected by the current pressure. The concept of such an instantaneous signal may be considered a current instant in time as in the current instant leak. The ventilation signal (VS) may be a minute ventilation (e.g., three minute) calculated by low pass filtering the patient flow. The processing of data to generate these signals is discussed in more detailed herein.

Figure 11:
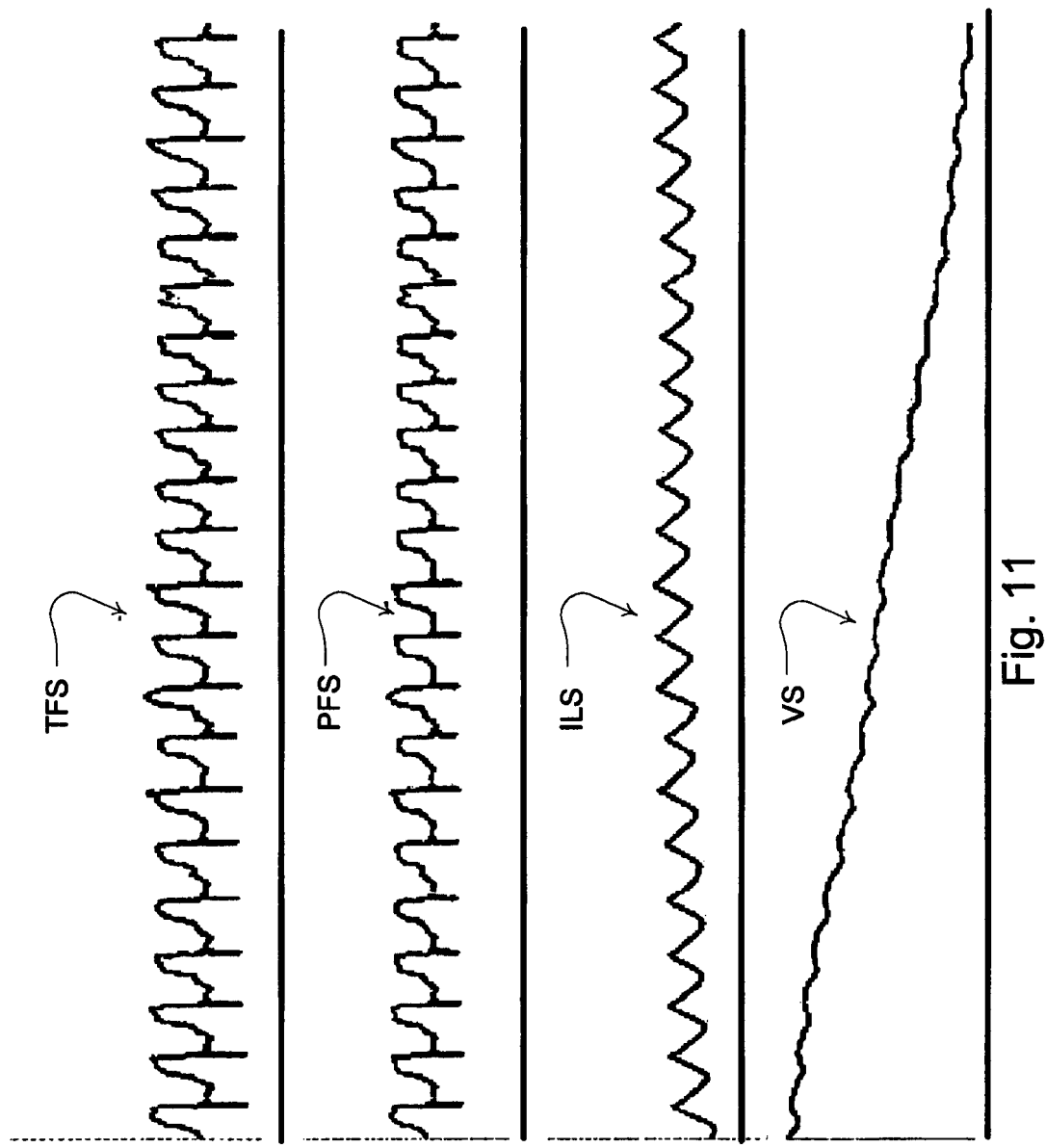
FIG. 11 is a graph that illustrates example flow based features that may be indicative of a valve-like mouth leak.

In this embodiment, the determination of a Valve Mouth Leak, such as by a processing algorithm, may be based on a patient flow signal. For example, by detecting a sharp negative peak that is typical of valve-like mouth leak. In such a case, an algorithm may measure the duration (in each breath) over which the patient flow is below a cut-off flow level during expiration. If this duration is very short, it may be considered a sharp negative peak and it is likely that VML is occurring. FIG. 11 illustrates data typical of an epoch captured during a period of a valve-like mouth leak. The sharp negative peak in early expiration is a so called 'valve-like' effect which happens when the mouth opens in early expiration. In FIG. 11, the illustrated total flow signal, patient flow signal, instantaneous leak signal and ventilation signals are comparable to the signals of FIG. 10.

(1) Processing Overview

Figure 12:
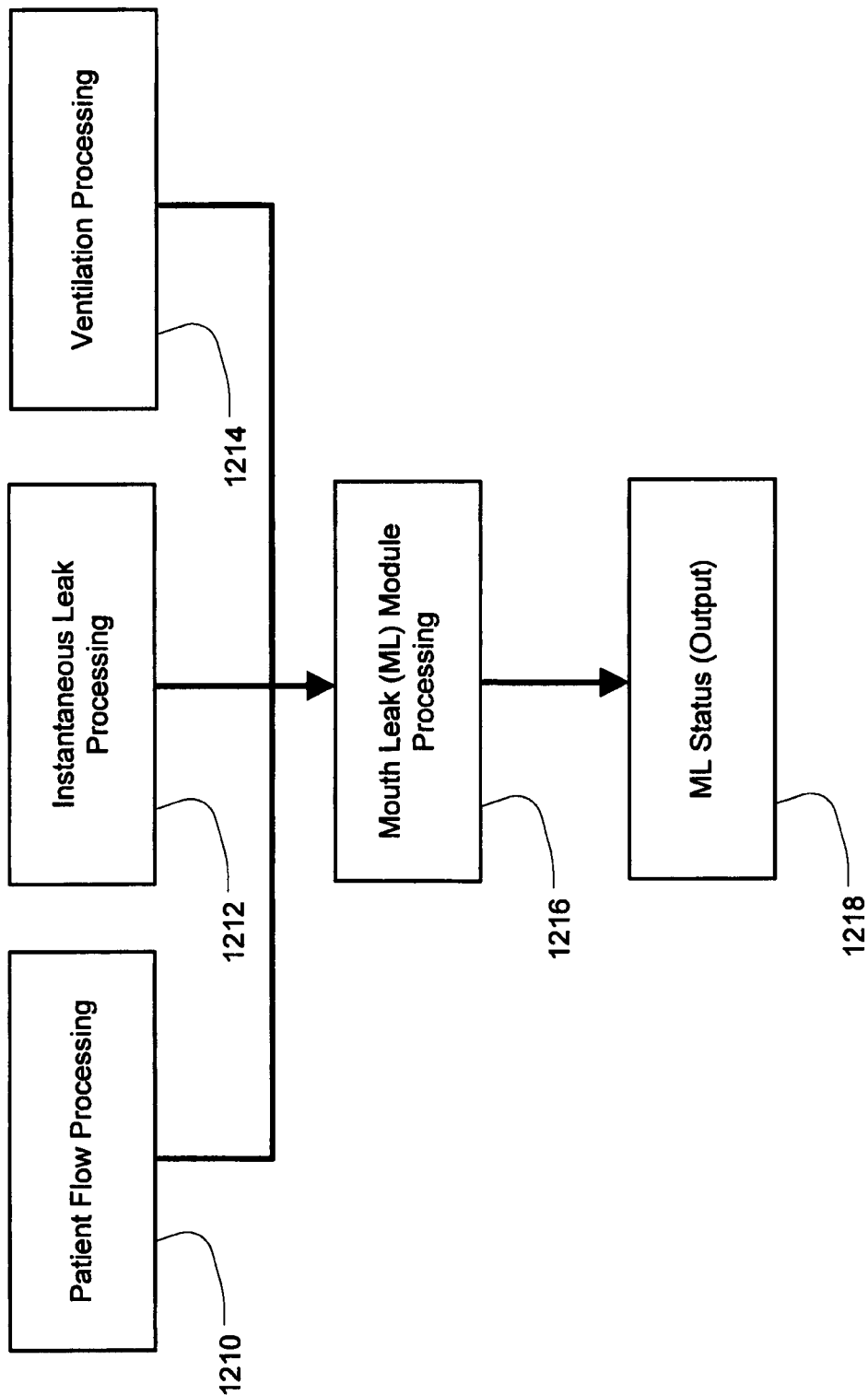
FIG. 12 is a processing module flow diagram in an embodiment suitable for detection of mouth leak events.

FIG. 12 is a high-level overview diagram of an example mouth leak detection processing algorithm. This algorithm may have three signal inputs: a patient flow signal from a patient flow signal processing 1210, a ventilation signal from a ventilation signal processing 1214 and an instantaneous leak signal from an instantaneous leak signal processing 1212. The mouth leak module processing 1216 performs calculations with these inputs and then reports mouth leak status information 1218, such as a binary True/False output indicative of a mouth leak.

(a) The processing involved in inputs 1210, 1212 and 1214 for this embodiment may be as follows:
1. Patient Flow or a patient flow signal: This may be a respiratory flow signal and may be a filtered measure from a flow sensor (at 1210);
2. Ventilation Flow or a ventilation flow signal
   This may be calculated or determined at 1214 as half of an integrated value of the absolute value of the patient flow signal over set period of time (e.g., three minutes) A three minute ventilation signal may be an integrated value of the patient flow signal over 3 minutes or 180 seconds.
3. Instantaneous Leak or an instantaneous leak signal: This may be calculated or determined in 1212 by the following process:
   Calculate a Mask Flow or mask flow signal by taking a Total Flow and subtracting a Vent Flow or vent flow signal. (The vent flow may be the flow through the vent of a vented mask used for Positive Airway Pressure Therapy).
   Calculate a Mean Mask Flow (also referred to as a Mean Leak) by low pass filtering the mask flow with a constant or variable time constant. (This may be considered effectively a 'DC' component or mean of the Mask Flow Signal.)
   Calculate the Mean Square Root Mask Pressure by square rooting current Mask Pressure and then filtering it with a low pass filter which can have a constant or variable time constant. Mask Pressure may be the measured pressure from a pressure sensor, such as one located at the flow generator of a respiratory treatment apparatus, that is adjusted (e.g., by subtraction) for a pressure loss due to the specific hose and mask used in delivering a pressure treatment such as a Positive Airway Pressure (PAP).
   Calculate the Instantaneous Leak by multiplying the mean mask flow by the current square root of mask pressure divided by the Mean Square Root Mask Pressure. Alternatively, instead of using the Instantaneous Leak, the originally calculated Mean Leak can be used in the described Mouth Leak calculation.

(b) Example Mouth Leak Module Processing

Figure 13:
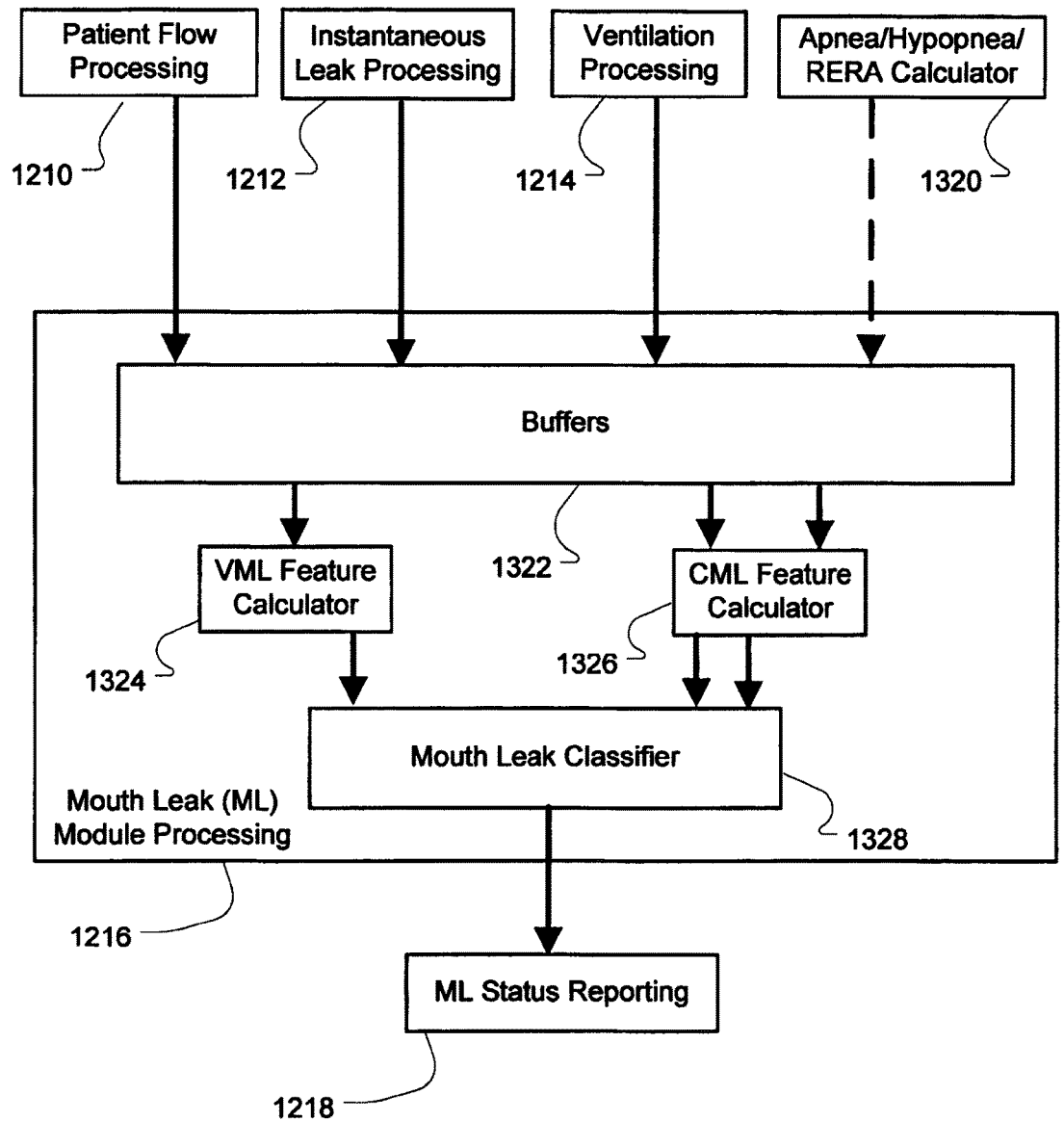
FIG. 13 is a further processing module flow diagram in an embodiment suitable for detection of mouth leak events.

The processing of the mouth leak module at 1216 may be further considered by the diagram of FIG. 13. The module at 1216 may be divided into four sub-module sections or sub-processing sections including buffer processing at 1322, VML feature calculation processing at 1324, CML feature calculation processing at 1326 and mouth leak classifier processing at 1328.

Buffer Processing at 1322

Buffers 1322 may be updated based on the data resulting from the Patient Flow Processing, Instantaneous Leak Processing or the Ventilation Processing at 1210 to 1214, respectively. Thus, the inputs for this processing may include signals representing Patient Flow, Ventilation and Leak. Outputs from this processing may include a Leak Buffer, Ventilation Buffer, Patient Flow Buffer. The Leak and Ventilation Buffers may be implemented to maintain a record of recent data such as the last number of seconds (e.g., about 120 seconds) of reported values. The input signals may be sampled, such as at a frequency of about 0.5 hz, to create the buffers. For example, the newest sample from each input signal may be added to the respective buffer every 2 seconds and the oldest sample may be removed since only a rough trend may be implemented. Other sample rates can also be used. The Patient Flow Buffer may be a circular buffer derived from the Patient Flow and may contain the flow for the current breath. An occurrence of apnea, hypopneas or RERA's may cause fluctuations in the respiratory signal, which may be confused with the occurrence of a Mouth Leak event. Because of that, in some embodiments the filling of the buffers may conditioned on or based on a detection of apnea, hypopnea and/or respiratory related arousals (RERA) event conditions. For example, if a respiratory event such as an Apnea, Hypopnea or RERA occurs, then samples may not be added to the ventilation and leak buffers for a period of time such as about 180 seconds in the event that a three minute ventilation signal is used as previously described. Moreover, during this apnea, hypopnea or RERA event, the mouth leak (ML) Status may be set to false during the event and for a period of time comparable to the time constant of the ventilation buffer.

CML Feature Calculation Processing at 1326

The processing of this module may calculate features indicative of presence of continuous mouth leak such as the Modified Covariance feature and/or a Covariance Sum feature as described in more detail herein. These may be based on input data including the Ventilation Buffer and/or Leak Buffer. The output may include a Modified Covariance signal and/or a Covariance Sum signal. The Modified Covariance and the Covariance Sum may be determined as described in more detail herein.

As previously described, with the ventilation and leak buffers denoted and $[(v=\{v\})_1, v_2, \ldots, v_n\}$ and $[(l=\{l\})_1, l_2, \ldots, l_n\}$ respectively, the covariance may be calculated using the following:

$$\text{cov}(v, l) = \overline{(v - \bar{v})(l - \bar{l})} = \frac{1}{n} \sum_{i=1}^{n} \left( v_i - \frac{\sum_i v_i}{n} \right) \left( l_i - \frac{\sum_i l_i}{n} \right)$$

This covariance may be multiplied by the sign of the gradient of the Leak buffer (l), to differentiate between the start (leak increasing) and finish (leak decreasing) of a Mouth Leak episode. The gradient may then be determined according to the following:

$$\text{grad}(l) = \sum_{i=1}^{N} [(l_i - \bar{l})(t_i - \bar{t})]$$

where:
l is the leak buffer;
$l_i$ is the $i_{th}$ leak value;
$\bar{l}$ is the mean of the leak buffer;
t is the interval over which the gradient is to be calculated ($t_i$=1, 2, ..., N); and
$\bar{t}$ is the mean of the interval t.

A "modified" covariance value (ModifiedCov) may be determined by the following formula:

ModifiedCov=sign(grad(l))×cov(v,l)

Finally, the Covariance Sum (CovSum) is calculated by summing the modified covariance (Cov) signal using the below equation. If the covariance (Cov) switches from positive to negative or vice-versa, then the covariance is set to 0 before continuing the summing.

CovSum$_i$=ModifiedCov$_i$×$t_{slow}$+CovSum$_{i-1}$

Where:
CovSum$_i$ is the covariance sum at the current instant of time;
CovSum$_{i-1}$ is the covariance sum at the previous instant of time;
ModifiedCov$_i$ is the Modified Covariance at the current instant of time; and
$t_{slow}$ may be a desired constant such as a value of 2.

Figure 14:
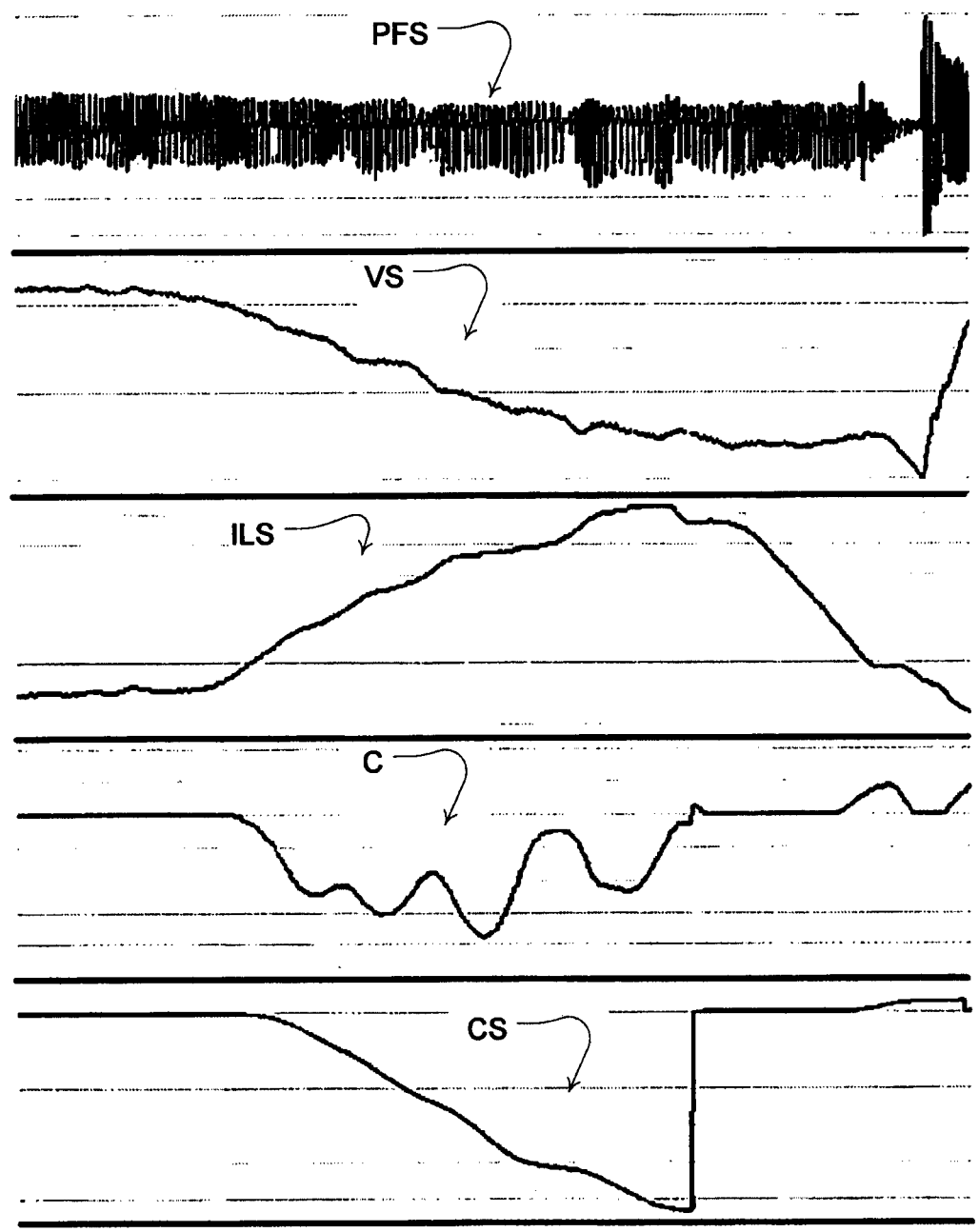
FIG. 14 is a signal graph showing various feature signals that may be implemented for detection of a continuous mouth leak event.

An illustration of the signals representing these CML features is shown in FIG. 14. These signals were calculated based on the patient flow signal ("PFS") during a continuous mouth leak period. As illustrated, the modified covariance signal (labeled as "C" in FIG. 14) will become negative if the instantaneous leak signal ("ILS") and ventilation signal ("VS") move in opposite directions at the same time and it will become positive if the signals move in the same direction at the same time. Thus, the covariance signal will go negative at the start of a mouth leak episode and at the end of a mouth leak episode. The covariance signal is multiplied by the gradient sign of the leak buffer in order to differentiate between start and finish of a mouth leak event (the gradient sign will be positive at the start of a mouth leak event and negative at the end of a mouth leak event. Therefore, the modified covariance signal will then be negative at the start of a mouth leak event and positive at the end of a mouth leak event). The covariance sum signal is labeled in FIG. 14 as signal "CS").

VML Feature Calculation Processing at 1324

The processing of this module evaluates the patient flow signal over one breath to determine whether a VML event is present or not in the breath. From the patient flow signal trace shown in FIG. 15, a breath with VML (shown on the left), the time spent below a flow $Q_{cutoff}$ is smaller than that for a normal breath (shown on right). In the example, the input to the module can be the patient flow buffer and the output feature may be a signal indicative of VML, referred to herein as a VML_Level. The feature may be determined by the following methodology.

Figure 15:
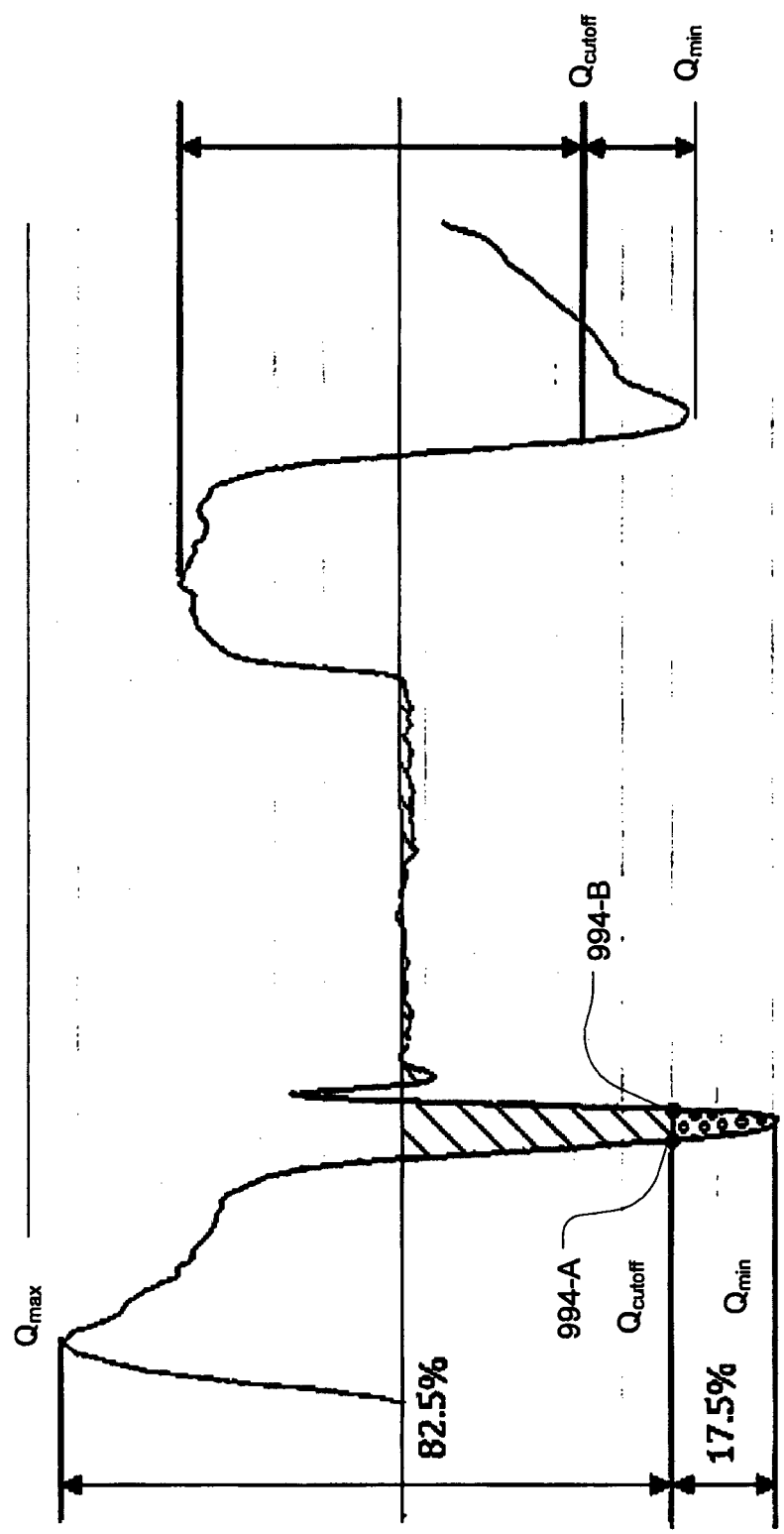
FIG. 15 is a signal graph of patient flow showing various features that may be implemented for detection of a valve-like mouth leak event.

Calculate the Total Expiratory Area. As illustrated in FIG. 15, this is the area highlighted with circles plus the area highlighted with stripes. Generally, the area below $Q_{cutoff}$ is the area with circles.

Calculate Area below $Q_{cutoff}$ (area highlighted with circles)

Calculate VML_RATIO by dividing area below $Q_{cutoff}$ by Total Expiratory Area (e.g., area of FIG. 15 with circles divided by the sum of area with circles and area with stripes)

IF VML_RATIO is below VML THRESHOLD, which may be preset to a value of 0.2, add 1 to VML_BUFFER. ELSE add 0 to the VML_BUFFER;

IF the sum of the VML_BUFFER is greater than a desired threshold such as 2, set VML_LEVEL to 2;

IF the sum of the VML_BUFFER is greater than 0 and less than or equal to 2, set VML_LEVEL to 1

IF the sum of the VML_BUFFER is equal to 0, then set VML_LEVEL to 0.

Figure 16:
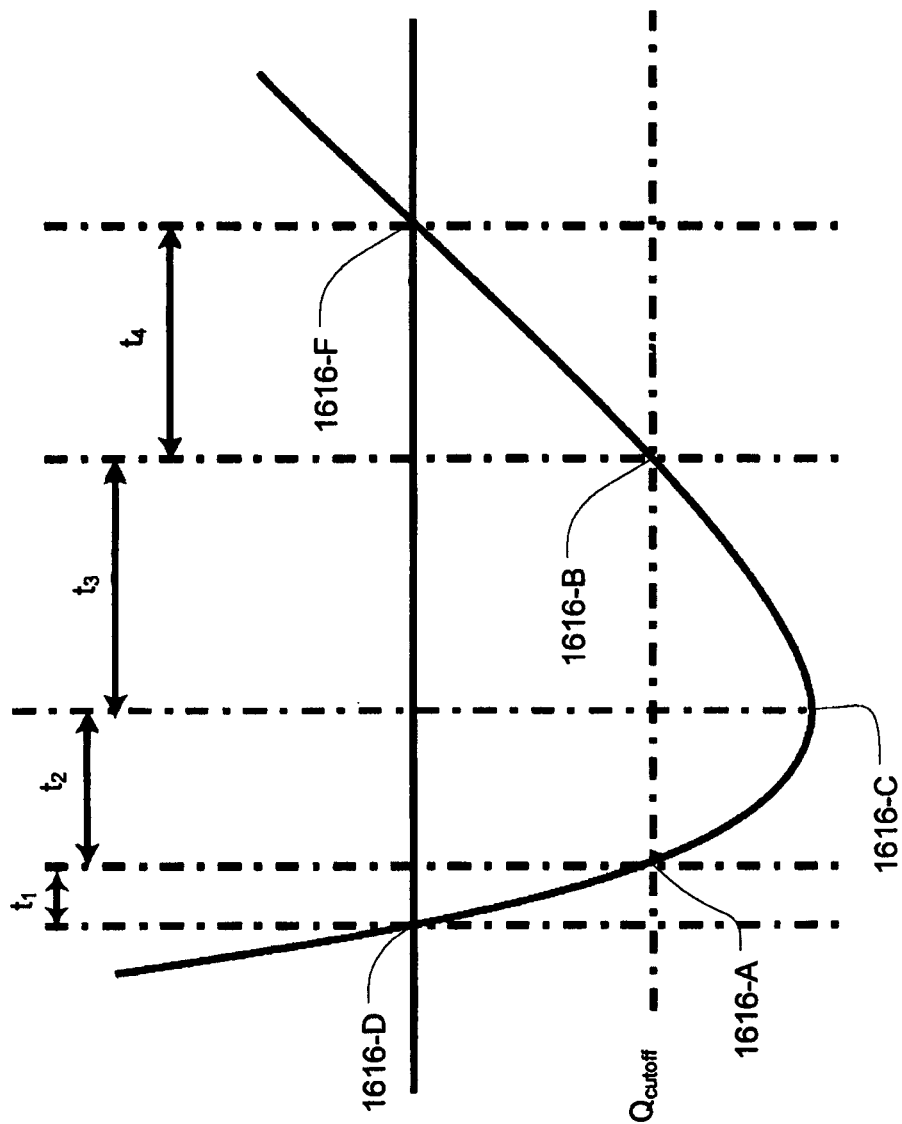
FIG. 16 is a further signal graph of patient flow showing alternative features that may be implemented for detection of a valve-like mouth leak event.

While this example methodology predicts the presence of VML by calculating a ratio of area below $Q_{cutoff}$ and the total expiratory area, other methods may also be implemented, such as a methodology based on the illustration of FIG. 16. FIG. 16 shows a patient expiratory flow section of a breath. In this example, an indication of VML may be obtained by calculating one or more time ratios. For example, the magnitude of ratios, such as $t_1/(t_1+t_2+t_3)$, $(t_1+t_2+t_3)/(t_1+t_2+t_3+t_4)$, and/or $(t_2+t_3)/(t_1+t_2+t_3+t_4)$ can be evaluated for this purpose. Such ratios may indicate a relative sharp rise (fall) of the peak and/or a relative narrow peak, thus providing an indication of VML.

Mouth Leak Classifier Processing at 1328

Figure 17:
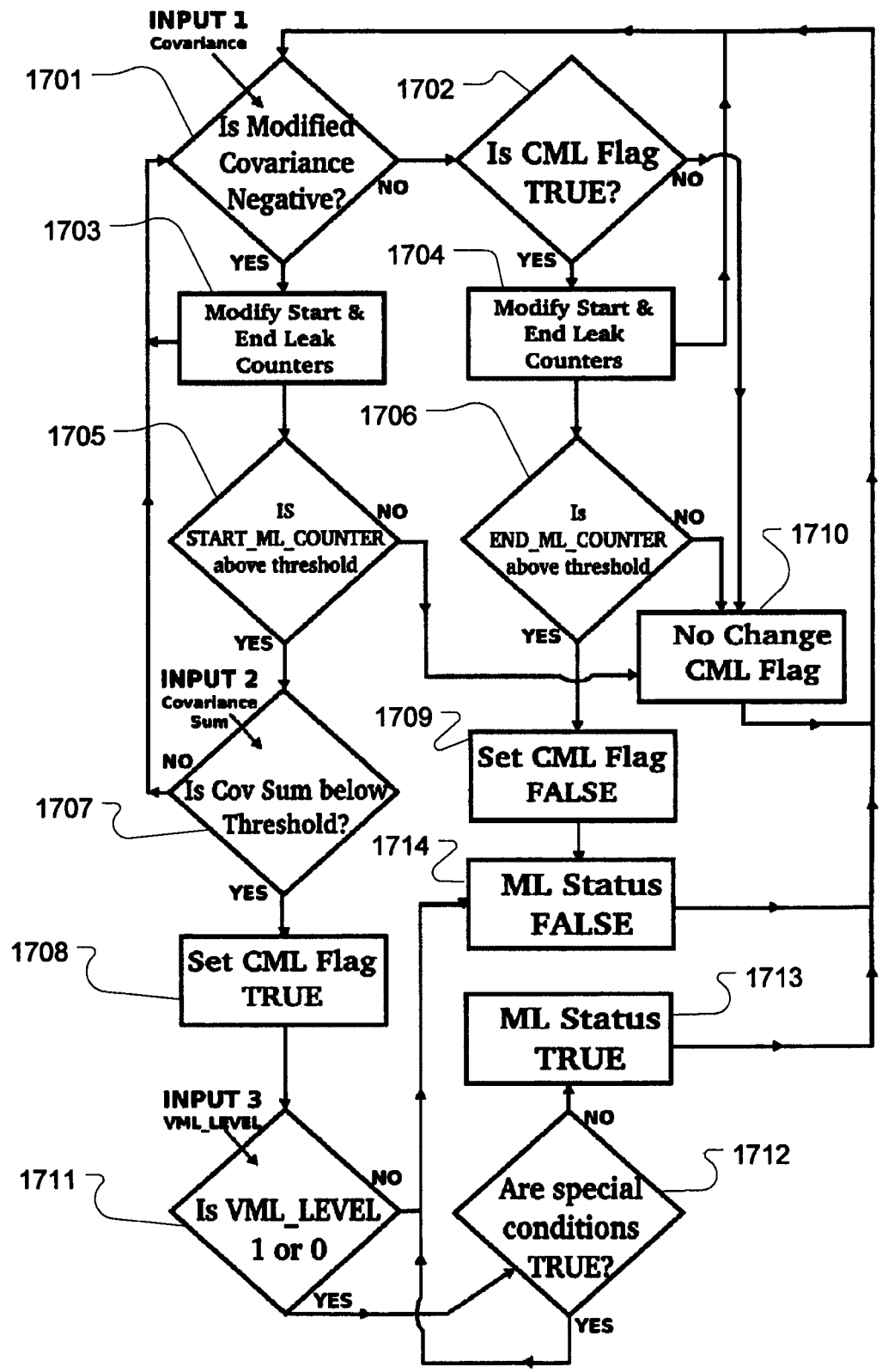
FIG. 17 is a flow chart of an example mouth leak detection module in some embodiments of the present technology.
Figure 17A:
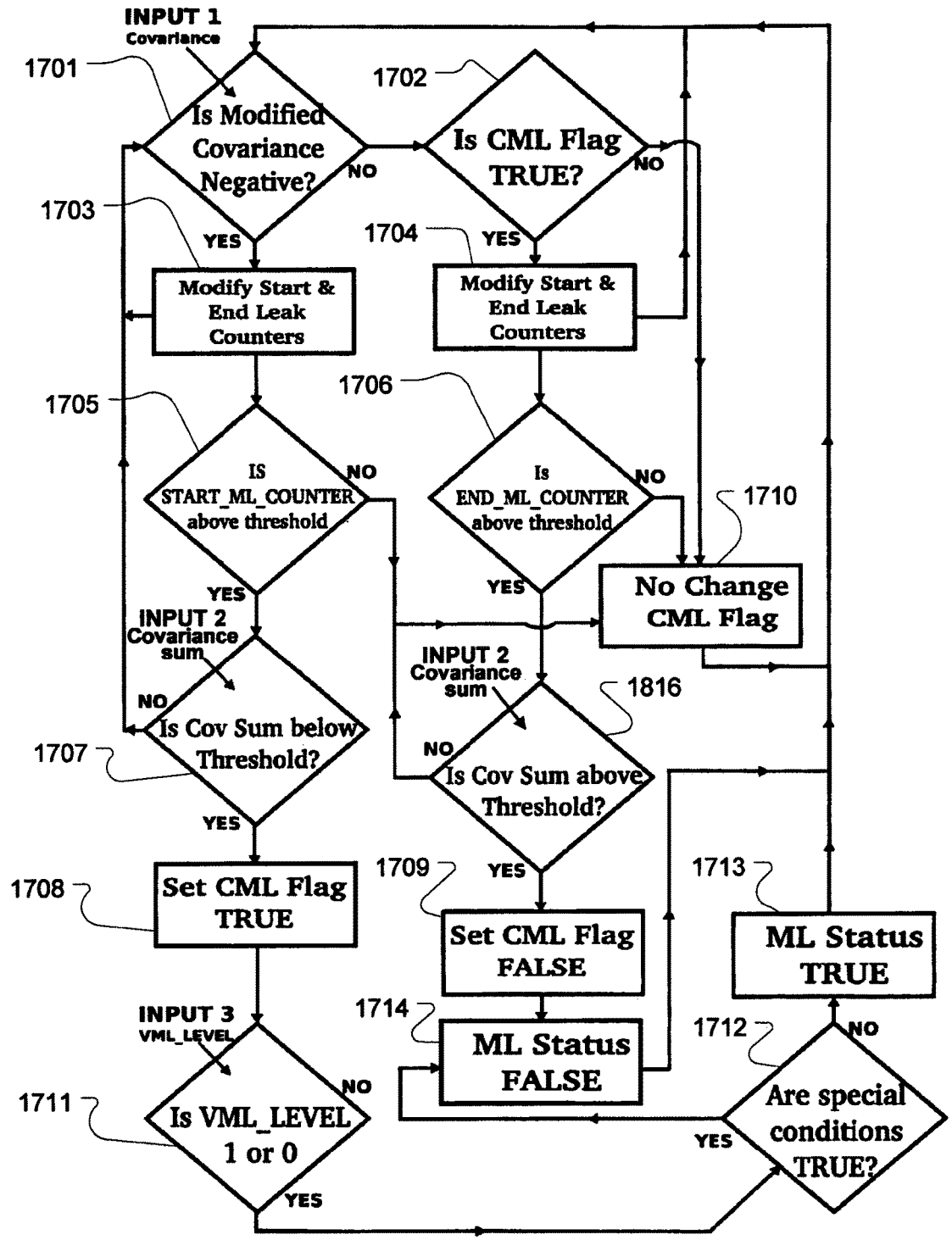
FIG. 17A is another flow chart of an example mouth leak detection module in some embodiments of the present technology.

This module classifies the mouth leak status. The inputs for this module include Modified Covariance and Covariance Sum (from 1326) and VML_LEVEL (from 1324). The output may be the current ML Status, which may be a flag or "ML" flag that indicates either TRUE or FALSE with respect to the status or presence of a mouth leak. An example flow chart for the processing of the module is illustrated in FIG. 17 or FIG. 17A.

The rules outlined in the ML Classification Table below may be implemented to classify the ML Status. In this embodiment, the rules are designed such that ML Status is TRUE ONLY if a CML Flag is TRUE and there is little or no VML (i.e., a VML_LEVEL is less than or equal to 1). Thus, the ML status variable may be considered an indicator of a mouth leak event that is continuous in nature and is based on an assessment that rules out the potential that it is a valve-like mouth leak event. Although it may be reported as output to a user, the VML_LEVEL itself does not necessarily need to be reported as it might have limited clinical relevance. However, it may also be useful for the control functions of the algorithms of a Flow Generator that may be based on detections of Mouth Leak. Thus, it may serve as a control input, such as, an input for a pressure treatment control of a respiratory treatment apparatus.

| ML Classification Table | | |
|---|---|---|
| | CML Flag = TRUE | CML Flag = FALSE |
| VML_LEVEL = 0 | ML Status = TRUE | ML Status = FALSE |
| VML_LEVEL = 1 | ML Status = TRUE | ML Status = FALSE |
| VML_LEVEL = 2 | ML Status = FALSE | ML Status = FALSE |

Thus, the module may also calculate a CML Flag that is evaluated in the setting of the ML flag. This CML flag is representative of Continuous Mouth Leak.

One embodiment for the processes for setting of the CML flag and ML status flag may be further considered in conjunction with the example process flow of the chart of FIG. 17. At 1701, a decision is made as to whether the current Modified Covariance is negative. If it is, then the process proceeds to 1703. If it is not, the process proceeds to 1702.

At 1702, if the CML flag is currently set to TRUE, then proceed to 1704. Otherwise, the CML flag is set to FALSE, so the process will proceed to 1710.

At 1703, if at the previous instant of time, the Modified Covariance flag was set to positive, an END_ML_COUNTER variable will be reset to 0 and a START_ML_COUNTER variable will be set to 1 (as this is the beginning of a new mouth leak 'possible' period) and the process will proceed to 1701. The END_ML_COUNTER variable is used to track the end of Mouth Leak Events. The process will wait for a certain time to elapse (e.g., the counter will need to reach a certain threshold) and then only set the CML FALSE flag. This can help to ensure that the process does not wrongly terminate detection of mouth leak events. The START_ML_COUNTER variable may be used to track the beginning of Mouth Leak Events. The process will wait for a certain time to elapse (e.g., the counter reaching a certain threshold) and then only set the CML TRUE flag. This may ensure that the process does not falsely identify mouth leak events. A Mouth Leak 'Possible' Period is the time during which the process initiates the Start Mouth Leak Detection counters but does not set the CML TRUE flag since the counters have not hit the necessary threshold and it is too early to decide if an actual mouth leak period has occurred. Otherwise at 1703, if at the previous instant of time, the Modified Covariance flag was set to negative and the system is already in a mouth leak 'possible' period, the process will continue to increment the START_ML_COUNTER variable and the process will proceed to 1705.

At 1704, if at the previous instant of time, the Modified Covariance flag was set to positive, the START_ML_COUNTER variable will be reset to 0 and the END_ML_COUNTER variable will be set to 1 (as this is beginning of a mouth leak 'possibly' ending period) and the process will proceed to 1701. A Mouth Leak 'Possibly' Ending Period is the time during which the process initiates the End Mouth Leak counters but does not set the CML FALSE flag as the counters have not hit the necessary threshold and it is too early to decide if the mouth leak period has actually ended. Otherwise at 1704, if at the previous instant of time the Modified Covariance flag was set to positive and the system is already in a mouth leak 'possibly' ending period, then continue to increment the END_ML_COUNTER variable and proceed to 1706.

At 1705, if the START_ML_COUNTER variable is above a threshold the process will proceed to 1707. Otherwise at 1705, the process will proceed to 1710. In this instance, the threshold may be any desired preset value (e.g., 30). Such a value may signify that the Mouth Leak 'Possible' Period has gone on long enough and that indeed a Mouth Leak event has occurred.

At 1706, if the END_ML_COUNTER variable is above a threshold, the process will proceed to 1709. Otherwise, the process will proceed to 1710. In this instance the threshold may be any desired preset value, (e.g., 30). It signifies that the Mouth Leak 'Possibly' Ending Period has gone on long enough and that indeed a Mouth Leak Event has just finished.

At 1707, the Covariance Sum is checked. If it is below a threshold, the process will proceed to 1708. Otherwise, the process will proceed to 1701. In this check, the threshold is implemented to assess whether the Covariance Sum is sufficiently small in order to warrant a period of Mouth Leak. This is to ensure that there is a significant enough change in ventilation and leak in order to classify a Mouth Leak Period as TRUE. The threshold may be any suitable preset value (e.g., −0.125).

At 1708, the CML Flag variable is set to TRUE and the process proceeds to 1711. At 1709, the CML Flag variable is set to FALSE and the process proceeds to 1714. At 1710, the process does not change the CML Flag and process proceeds to 1701.

At 1711, the VML_level variable is checked. If the variable is low then the process proceeds to 1712. Otherwise at 1711, if the variable is not low, the process proceeds to 1714. The VML_LEVEL may be considered 'low' if there is little or no valve like mouth leak. One or more thresholds may be implemented for the 'low' check. For example, in the present implementation, if the VML_LEVEL variable is either 1 or 0 then it is considered 'low'. If the VML_LEVEL variable is 2, then it is considered sufficiently high to not classify Mouth Leak.

At 1712, some additional conditions may be checked. For example, the following two conditions A and B (described below) may be evaluated and if either one is true the process returns a TRUE and proceeds to 1714. Otherwise at 1712, the process will proceed to 1713.

In such a check at 1712, the two conditions (Condition A and Condition B) may be as follows:

Condition A: IF current ventilation value is greater than a threshold (e.g., about 95%) of a START_VENTILATION value AND an oldest ventilation value in the ventilation buffer is greater than the START_VENTILATION, THEN return TRUE.

Condition B: IF the current leak value is less than a threshold (e.g., about 105%) of the START_LEAK value AND the oldest value in the leak buffer is greater than START_LEAK value, THEN return TRUE.

At 1713, the process sets the ML Status flag variable to TRUE and proceeds to 1701. At 1714, the process sets the ML Status variable to False and proceeds to 1701.

Another embodiment for the processes involved in setting of the CML flag and ML status flag may be considered in conjunction with the example process flow in the chart of FIG. 17A. The processes of FIG. 17A are comparable to the processes of FIG. 17. However, an additional check at 1816 is implemented in the version of FIG. 17A. In this embodiment, as a result of the threshold comparison at 1706, if the END_ML_COUNTER is above the threshold, the process proceeds to 1816. At 1816, the covariance sum is checked such as by comparing it to a threshold. If the covariance sum is above the threshold, the process advances to 1709. However, if it is not above the threshold, the process advances to 1710. This check of the covariance sum at 1816 may represent a determination of whether or not the mouth leak event has ended. If the covariance sum is sufficiently large, it is taken as an indication that the mouth leak event has ended. The threshold for such a check may be any suitable preset value (e.g., 0.125).

D. Example Leak Severity Analysis

In addition to the leak event related data determined by the previous methodologies, such as the VML duration and the CML duration and counts of such events, a combined measure of leak severity may be based on the detection of several measures that quantify different types of leak events. For example, such a measure may be a leak severity index that may be determined, recorded and/or reported by the detector to a user or physician. In one embodiment, which may optionally employ a fuzzy logic analysis, a single leak severity index is determined based on both CML and VML durations. A text message concerning the severity may also be provided (e.g., "high", "very high", "low", etc.)

In such an embodiment, the durations of the CML events may be summed to provide a total duration of the CML events during, for example, a treatment session or a sleep session. Similarly, the durations of the VML events may be summed to provide a total duration of the VML events. These durations may then be converted to a proportion of the total treatment time or sleep session time during which the leak events were detected or the treatment apparatus was utilized. For example, if multiple CML events accounted for four hours of an eight hour sleep session, the duration of CML may be represented as 50%. In some embodiments, the total time of the treatment session may optionally represent multiple sessions.

Figure 18:
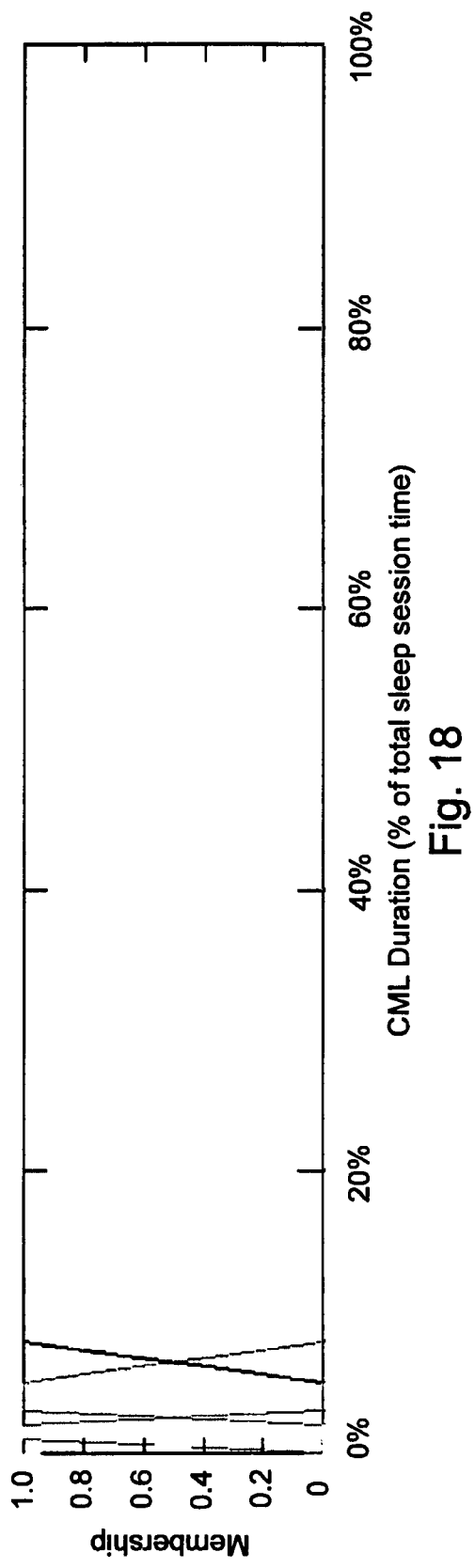
FIG. 18 is a graph of example membership functions for continuous mouth leak events for quantifying leak severity based on leak duration.
Figure 19:
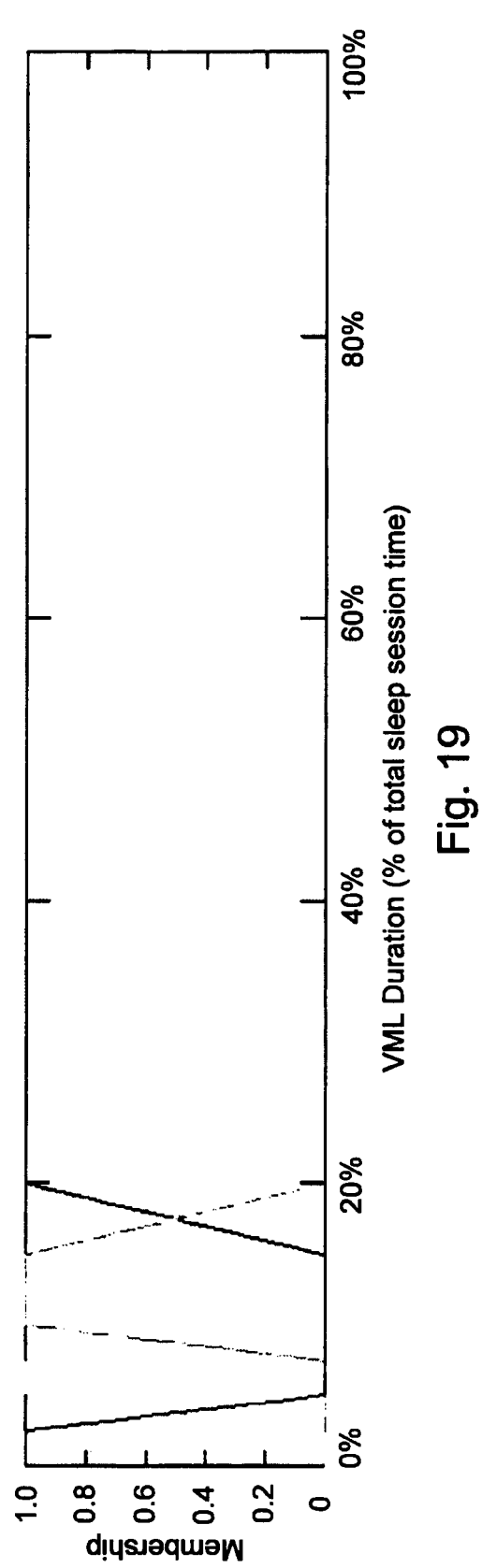
FIG. 19 is a graph of example membership functions for valve-like mouth leak events for quantifying leak severity based on leak duration.

In the fuzzy logic example, the processor may then process durations for the different detected leak events (e.g., the percent duration of CML events ($l_c$) and percent duration of VML events ($l_v$)) as fuzzy sets. In this regard, example membership functions are illustrated in FIGS. 18 and 19. For both $l_v$ and $l_c$, shown in FIGS. 18 and 19 respectively, there are four 'fuzzy sets', or categories labelled as follows: low, medium, high, and very high. Any measurement of $l_v$ or $l_c$ can belong to any one of these sets, or may be partly in two sets. For example, an $l_v$ measurement of 20% may be considered somewhere between high and very high and would fall partly into both categories. The degree to which a certain measurement belongs to a certain set or category is given by the membership function of the fuzzy set.

Thus, the output for each function will be a value between 0 and 1. In this regard, although other functions are possible, in this example, each membership function is asymmetric, and includes (a) an interval over which the membership value is equal to 1; (b) an interval(s) over which the membership value is equal to 0 and (c) linear piecewise-continuous segments in between.

The example functions are defined in Table A.

TABLE A

|  | CML Duration (%) | VML Duration (%) |
|---|---|---|
| Low | $\mu(x) = \begin{cases} 0 \leq x \leq 1, & 1 \\ 3 \leq x \leq 100, & 0 \end{cases}$ | $\mu(x) = \begin{cases} 0 \leq x \leq 2, & 1 \\ 5 \leq x \leq 100, & 0 \end{cases}$ |
| Medium | $\mu(x) = \begin{cases} 0 \leq x \leq 1, & 0 \\ 3 \leq x \leq 5, & 1 \\ 7 \leq x \leq 100, & 0 \end{cases}$ | $\mu(x) = \begin{cases} 0 \leq x \leq 2, & 0 \\ 4 \leq x \leq 7, & 1 \\ 10 \leq x \leq 100, & 0 \end{cases}$ |
| High | $\mu(x) = \begin{cases} 0 \leq x \leq 7, & 0 \\ 7 \leq x \leq 10, & 1 \\ 15 \leq x \leq 100, & 0 \end{cases}$ | $\mu(x) = \begin{cases} 0 \leq x \leq 7, & 0 \\ 10 \leq x \leq 15, & 1 \\ 20 \leq x \leq 100, & 0 \end{cases}$ |
| Very High | $\mu(x) = \begin{cases} 0 \leq x \leq 10, & 0 \\ 15 \leq x \leq 100, & 1 \end{cases}$ | $\mu(x) = \begin{cases} 0 \leq x \leq 15, & 0 \\ 20 \leq x \leq 100, & 1 \end{cases}$ |

Figure 20:
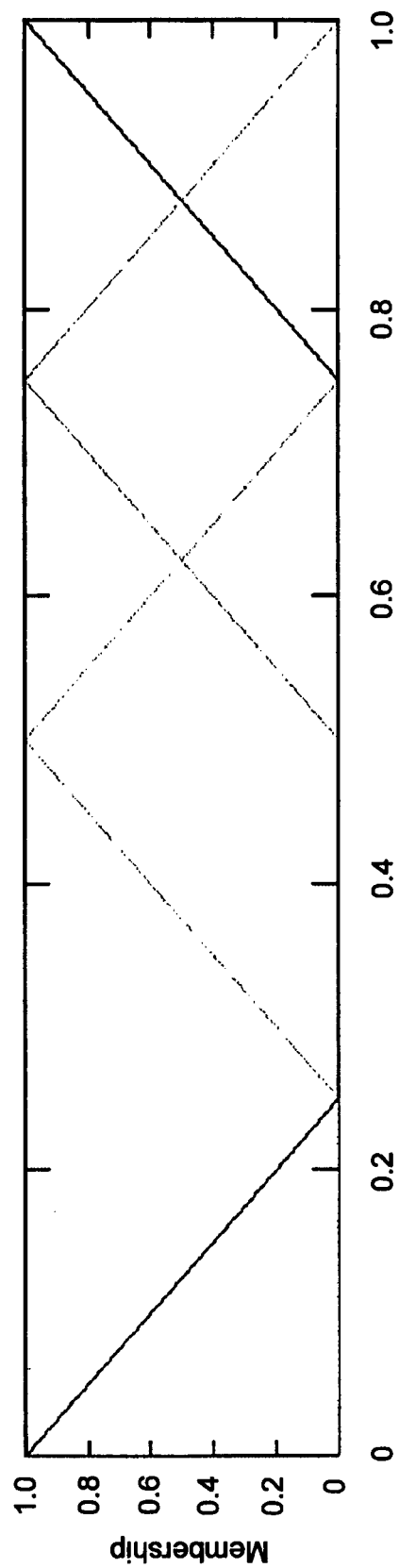
FIG. 20 is a graph of example output functions for quantifying leak severity based on different types of leak events.

In this example, there are also five output sets which may be labeled: very low, low, medium, high and very high. Example membership functions for these sets are illustrated in FIG. 20. In this embodiment, each output membership function is symmetric, and includes (a) a single point for which the membership value is equal to 1; (b) intervals over which the membership value is equal to 0 and (c) linear piecewise-continuous segments in between.

These example functions are defined in Table B.

TABLE B

|  | ML Index |
|---|---|
| Very Low | $\mu(x) = \begin{cases} x \leq -0.25, & 0 \\ x = 0, & 1 \\ x \geq 0.25, & 0 \end{cases}$ |
| Low | $\mu(x) = \begin{cases} x \leq 0, & 0 \\ x = 0.25, & 1 \\ x \geq 0.5, & 0 \end{cases}$ |
| Medium | $\mu(x) = \begin{cases} x \leq 0.25, & 0 \\ x = 0.5, & 1 \\ x \geq 0.75, & 0 \end{cases}$ |
| High | $\mu(x) = \begin{cases} x \leq 0.5, & 0 \\ x = 0.75, & 1 \\ x \geq 1.0, & 0 \end{cases}$ |
| Very High | $\mu(x) = \begin{cases} x \leq 0.75, & 0 \\ x = 1, & 1 \\ x \geq 1.25, & 0 \end{cases}$ |

To map the inputs to output, there may be a number of rules such as the following:

Rule 1—Low $l_c$ and low $l_v$ gives an output of VERY LOW.

Rule 2—Low $l_c$ and very high $l_v$ gives an output of MEDIUM.

[ . . . ]

Rule 16—Very high $l_c$ and very high $l_v$ gives an output of VERY HIGH.

These rules may be taken to define a rule table for determining which combination of input sets leads to which output set. An example of such a rule table is summarized in Table C.

TABLE C

| | | Valve leak | | | |
|---|---|---|---|---|---|
| | | Low | Medium | High | Very High |
| Continuous Leak | Low | Very Low | Very Low | Low | Medium |
| | Medium | Very Low | Low | Medium | High |
| | High | Low | Medium | High | Very High |
| | Very High | Medium | High | Very High | Very High |

The following fuzzy logic functions may be applied in determining the output index. In general, it may be assumed that for any variable x, the membership in set A is denoted by $\mu_A(x)$, and for any variable y, the membership in set B is denoted by $\mu_B(y)$. Based on thereon, the following logic functions may be evaluated.

Fuzzy AND $x$ AND $y = \min(\mu_A(x), \mu_B(y))$

Fuzzy OR $x$ OR $y = \max(\mu_A(x), \mu_B(y))$

Fuzzy NOT

NOT $x = 1 - \mu_A(x)$

With these fuzzy logic functions, a fuzzy rule-based classification may be performed. Generally, the variables for CML duration (e.g., percent of total session) and VML duration (e.g., percent of total session) may be denoted $x_c$ and $x_v$ respectively with fuzzy sets $A_c$ and $A_v$, and the output variable may be denoted y~[0,1] with fuzzy set B. Also, the measured value for each of these durations may be denoted as $l_c$ and $l_v$. Based on the contributions of all sixteen rules, the processing of the detector may generate the severity index according to a total output membership function $\mu_{tot}(y)$. To this end, the contribution of each rule may be given by:

$\mu_{out_i}(y) = \max(\min(\mu_{A_c}(x_c), \mu_{A_v}(x_v)), \mu_B(y))$

Each contribution may then be combined with a fuzzy AND to obtain the final output membership function. Finally, the centroid of this membership function may be implemented to determine a final output value suitable for use as a severity index (e.g., a value between 0 and 1, inclusive).

D. Example Architecture

Figure 21:
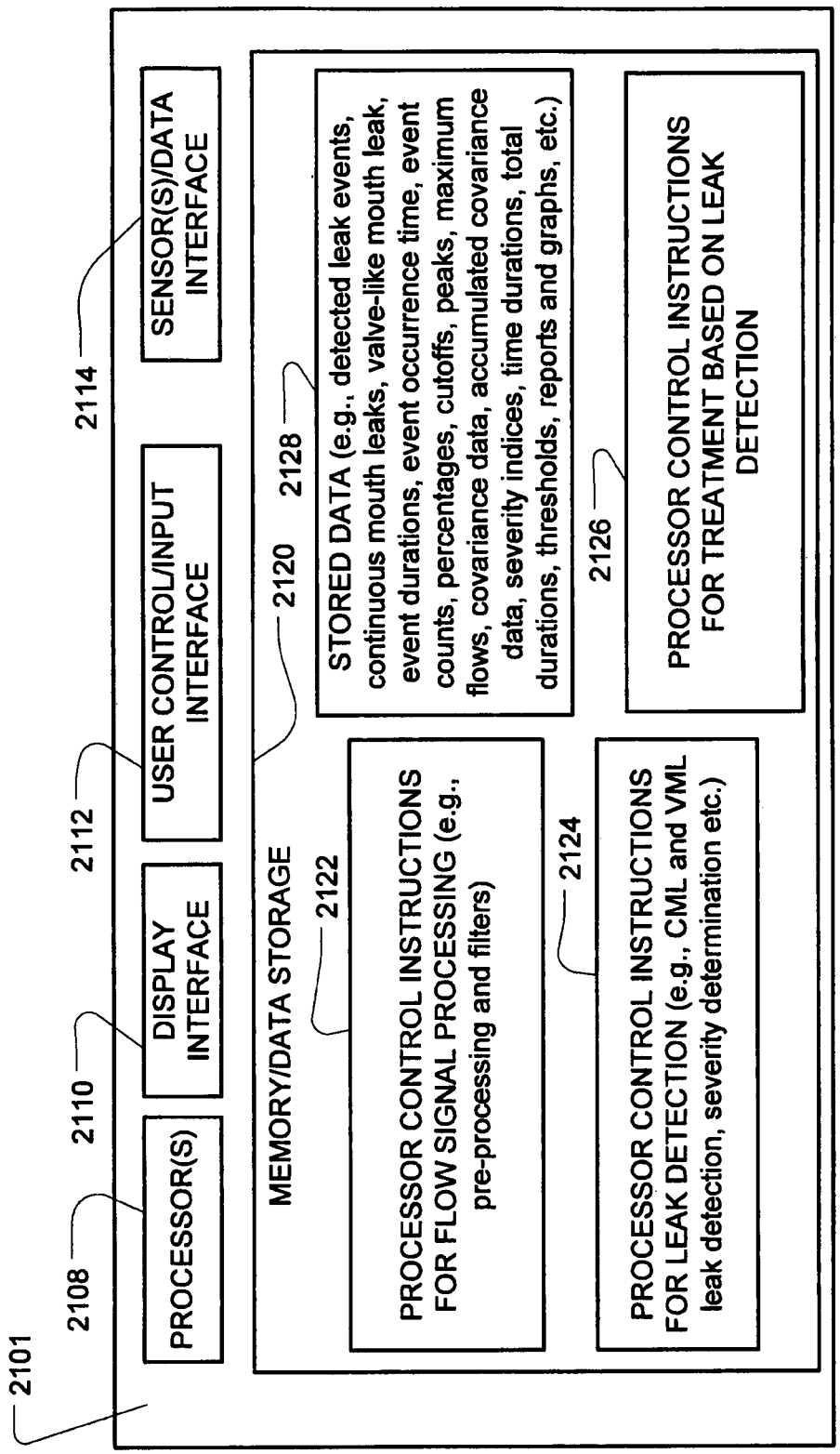
FIG. 21 is a block diagram of an example controller in a leak detection apparatus including example components thereof suitable for implementing the detection methodologies of the present technology.

An example system architecture of a controller that may implement the leak detector 102 is illustrated in the block diagram of FIG. 21. In the illustration, the leak detection device 2101 or general purpose computer may include one or more processors 2108. The device may also include a display interface 2110 to output leak detection reports (e.g., leak counts and/or severity measures such as the data illustrated in FIG. 1), results or graphs (e.g., any of the signal traces illustrated in FIG. 6 or 9) as described herein such as on a monitor or LCD panel. A user control/input interface 2112, for example, for a keyboard, touch panel, control buttons, mouse etc. may also be provided to activate the methodologies described herein. The device may also include a sensor or data interface 2114, such as a bus, for receiving/transmitting data such as programming instructions, flow data, leak detection data, leak related data, etc. The device may also typically include memory/data storage components containing control instructions of the aforementioned methodologies. These may include processor control instructions for flow signal processing (e.g., pre-processing methods, filters, buffers, instantaneous leak measures, ventilation measures etc.) at 2122 as discussed in more detail herein. They may also include processor control instructions for leak detection (e.g., CML detection, VML detection, covariance calculation, accumulated covariance calculations, cutoff calculations, severity index determination etc.) at 2124. They may also include processor control instructions for treatment control based on the leak detection at 2126. Finally, they may also include stored data 2128 for these methodologies such as detected leak events, continuous mouth leaks, valve-like mouth leaks, event durations, event occurrence times, event counts, percentages, cut-offs, peaks, maximum flows, covariance data, accumulated covariance data, severity indices, time durations, total durations, thresholds, reports and graphs, etc.)

In some embodiments, the processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer.

E. Example Pressure Treatment Control Process

Figure 22:
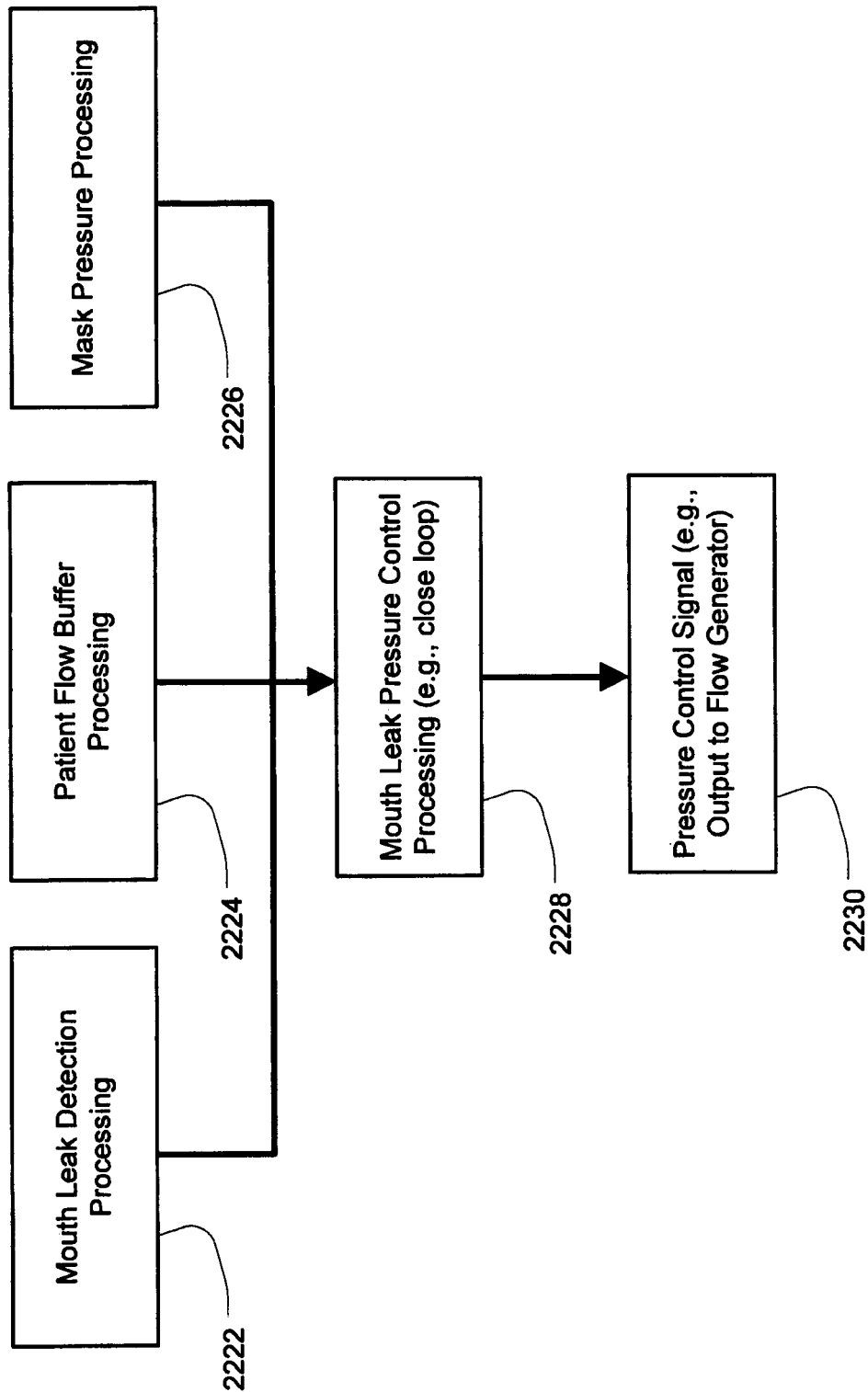
FIG. 22 is a block diagram showing some components for a respiratory treatment apparatus having leak detection and leak control of the present technology.

As previously mentioned, some embodiments of the aforementioned methodologies may be implemented in the control of a pressure treatment, such as a positive airway pressure, by a respiratory treatment apparatus. One such example embodiment is illustrated with reference to FIGS. 22 and 23. Such an embodiment may include a mouth leak pressure control processing module 2228, such as a mouth leak closed loop module, that controls pressure settings based on an output signal of a mouth leak detection module as illustrated in FIG. 22. In such an embodiment, the controller may servo-control pressure as a function of the detected leak signal to reduce or eliminate the leak as represented by the output signal(s) of the leak detection module.

For example, in the embodiment of FIG. 22, the module may be configured to generate signals to issue a change in therapeutic pressure based on the current Mouth Leak (ML) status. In some embodiments, if the ML Status variable as previously described is TRUE, a pressure setting may be adjusted. The pressure setting may either be increased or decreased in order to abolish the leak event represented by the ML status variable.

In controlling such pressure changes, the pressure control processing module 2228 may receive various input signals. For example, mouth leak detection processing 2222 may generate a leak detection signal, such as the Mouth Leak Status variable as previously described that may be representative of the detection of a continuous mouth leak event. Optionally, a Patient Flow Buffer processing 2224 module, such as a processing component that generates a patient flow buffer as previously described, may provide an updated buffer with recent patient flow data to the pressure control processing module 2228. Similarly, a mask pressure processing module 2226 may generate a signal indicative of mask pressure for the pressure control processing module 2228). For example, a measured pressure signal from a pressure sensor in the mask or in a Flow Generator may provide a suitable signal. The signal may be filtered and it may be adjusted to account for any pressure drop attributable to a patient interface and then be provided to the pressure control processing module 2226.

One example methodology of the pressure control processing module 2228 may be based on the current ML (Mouth Leak) status variable. If the module detects that the Mouth Leak status variable is TRUE (e.g., a continuous mouth leak event is detected), a probability calculation may be made. Such a probability may be considered a leak adjustment probability. For example, such a probability may be implemented with an ML_Closed_Loop_Probability variable. The probability may be a measure of the direction in which the current therapeutic pressure should be changed in response to the ML Status variable (e.g., if the ML Status is TRUE, should the pressure be increased or decreased in order to abolish the associated leak event?) For example, if the probability is greater than some threshold value (e.g., 0.5), then a pressure rise would be issued. If the probability is less than some threshold value (e.g., 0.5), a pressure decrease would be issued.

In one example, the ML_Closed_Loop_Probability may be calculated as a function of the current patient flow buffer. As previously described, this buffer may contain flow for a recent breath (i.e., one respiratory cycle) and may be considered a "breath profile". The probability may then be calculated with features of the breath profile such as its shape, the tidal volume, inspiratory time, etc. which can be indicative of the pressure being too low or too high.

Optionally, if the probability calculated is greater than the threshold (e.g., about 0.5), a pressure rise control signal may be issued such as one having a constant rate (e.g., a rate of 0.5 cm $H_2O$/second). Optionally, this rate may also be a function of the magnitude of the current leak signal (e.g., a value that quantifies a degree of the detected continuous mouth leak that triggered the setting of the ML status variable) and/or the probability itself. If the probability is less than the threshold (e.g., about 0.5), a pressure decrease may be issued at a constant rate (e.g., a rate of 0.5 cm $H_2O$/second). Optionally, this rate may also be a function of the magnitude of the current leak signal and/or the probability itself.

Figure 23:
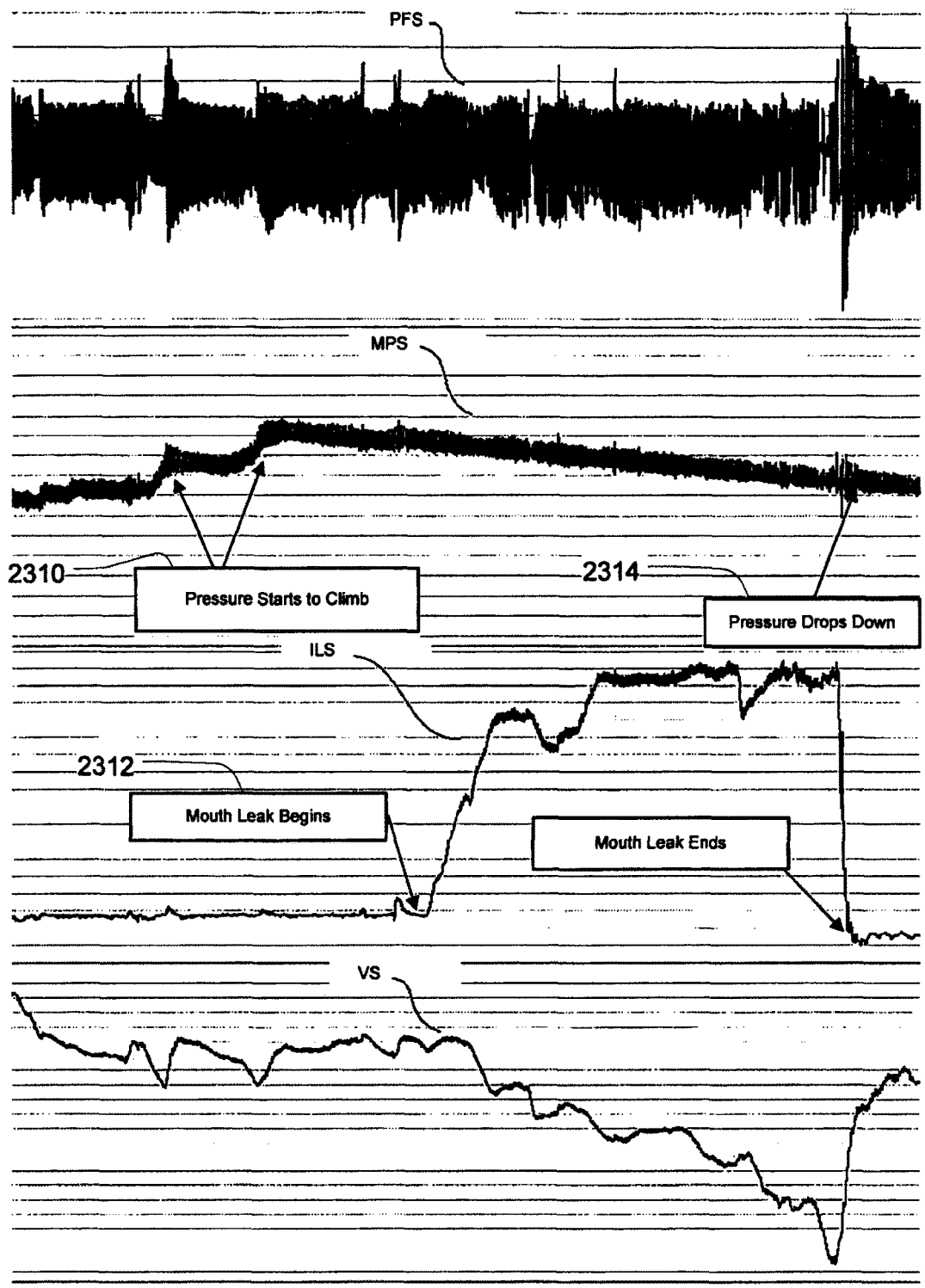
FIG. 23 is a signal graph illustrating leak based pressure control with the example control components of FIG. 22.

An example of the leak control that may be implemented by the mouth leak pressure control processing module 2228 is shown in FIG. 23. The figure contains several signals on a common time scale including, a patient flow signal (PFS), a mask pressure signal (MPS), an instantaneous leak signal (ILS) and a ventilation signal (VS). In FIG. 23, a sharp rise in pressure shown at 2310 creates a mouth leak shown at 2312. Based on the leak detection and the probability assessment, the mouth leak pressure control processing module 2228 generates a reduction in pressure until the reduction in pressure permits the mouth leak to fade away as shown at 2314. At this time, the leak is no longer detected and the controlled reduction to pressure ceases based on the leak detection.

In the foregoing description and in the accompanying drawings, specific terminology, equations and drawing symbols are set forth to provide a thorough understanding of the present technology. In some instances, the terminology and symbols may imply specific details that are not required to practice the technology. For example, although the terms "first" and "second" have been used herein, unless otherwise specified, the language is not intended to provide any specified order but merely to assist in explaining distinct elements of the technology. Furthermore, although process steps in the detection methodologies have been illustrated in the figures in an order, such an ordering is not required. Those skilled in the art will recognize that such ordering may be modified and/or aspects thereof may be conducted in parallel.

Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology. For example, although fuzzy logic has been implemented to combine data from various different detected leaks, other methods may be employed to generate a severity index that is based on detected quantifications of different types of leak.

Furthermore, it should be clear that the described method can not only be implemented by calculating various features based on the instantaneous values of the measured Flow and Leak, but the calculations can also be based on mean values that are averaged over a predetermined amount of time, such as a minute, three minutes etc.

In addition, the tests implemented in some of the described embodiments are of relative nature. For example, whilst the test at 1707 in FIG. 17 tests if a Coy Sum is "below" a certain threshold, this is based on the fact that the tested covariance sum is negative. Thus similar test may be applied to the absolute values of the respective values, in which case it will verify if the current value of the Cov Sum is "larger" than the respective threshold.

The invention claimed is:

1. A method for controlling a processor to detect leak from a flow of breathable gas within a respiratory pressure treatment apparatus, the method comprising:
   measuring the flow using a sensor; and
   in the processor:
      determining a ventilation measure and a leak measure from the measured flow;
      analyzing a covariance signal from the ventilation measure and the leak measure to detect a contemporaneous change comprising a change in the ventilation measure contemporaneous with a change in the leak measure;
      identifying a continuous mouth leak event based on the contemporaneous change; and
      controlling a respiratory therapy provided with the flow of breathable gas generated by the respiratory pressure treatment apparatus based on the covariance signal.

2. The method of claim 1 wherein the contemporaneous change comprises an increase in the measure of leak and a decrease in the measure of ventilation.

3. The method of claim 1 wherein the contemporaneous change comprises a decrease in the measure of leak and an increase in the measure of ventilation.

4. The method of claim 1 further comprising analyzing the ventilation measure and the leak measure to detect a further contemporaneous change comprising a further change in the ventilation measure contemporaneous with a further change in the leak measure.

5. The method of claim 4 further comprising determining a duration of the continuous mouth leak event, the duration beginning with the contemporaneous change and ending with the further contemporaneous change.

6. The method of claim 1 wherein the measure of ventilation comprises a low pass filtered absolute value of the measured flow divided in half, and wherein the measure of leak comprises an instantaneous leak determined as a function of a calculated leak conductance.

7. The method of claim 1 wherein the analyzing further comprises determining a gradient with data representative of the leak measure.

8. The method of claim 7 wherein the analyzing further comprises integrating a product of the sign of the gradient and the covariance.

9. The method of claim 8 wherein the identifying the continuous mouth leak event comprises scoring a continuous mouth leak event based on a comparison of the integrated product with a threshold.

10. The method of claim 1 further comprising controlling an adjustment to a pressure treatment based on the identified continuous mouth leak event.

11. The method of claim 1, the method further comprising: determining a plurality of features from the ventilation measure and the leak measure; analyzing in the processor the plurality of features with a time threshold and a magnitude threshold; and based on the analysis, setting a leak indicator, the leak indicator representative of the continuous mouth leak event.

12. The method of claim 1 further comprising:
measuring pressure and flow attributable to a breathable gas generated at a pressure above atmospheric pressure;
detecting a leak event based on an analysis of a measured flow signal; and
adjusting a therapeutic pressure as a function of the magnitude of the detected leak event, the adjustment for reducing the detected leak event.

13. The method of claim 1 wherein the ventilation measure is determined from samples of the measured flow over a period of time.

14. The method of claim 1 wherein the ventilation measure is determined based on an absolute value of the measured flow.

15. The method of claim 1 wherein the ventilation measure and the leak measure are applied to a leak module to detect the contemporaneous change, and wherein data representing the contemporaneous change is applied to a mouth leak classifier module configured to identify the continuous mouth leak event based on the contemporaneous change and a plurality of stored threshold values.

16. The method of claim 1 wherein the processor determines whether or not to adjust a pressure of the flow of breathable gas based on the covariance signal indicating a negative covariance.

17. A leak detection apparatus comprising:
a controller having at least one processor to access data representing a measured flow of breathable gas measured with a sensor, the flow of breathable gas provided with a respiratory pressure treatment apparatus, the controller being further configured to:
determine a ventilation measure and a leak measure from the measured flow;
analyze a covariance signal from the ventilation measure and the leak measure to detect a contemporaneous change comprising a change in the ventilation measure contemporaneous with a change in the leak measure;
identify a continuous mouth leak event based on the contemporaneous change; and
control a respiratory therapy provided with the flow of breathable gas generated by the respiratory pressure treatment apparatus based on the covariance signal.

18. The apparatus of claim 17 wherein the contemporaneous change comprises an increase in the measure of leak and a decrease in the measure of ventilation.

19. The apparatus of claim 17 wherein the contemporaneous change comprises a decrease in the measure of leak and an increase in the measure of ventilation.

20. The apparatus of claim 17 wherein the controller is further configured to analyze the ventilation measure and the leak measure to detect a further contemporaneous change comprising a further change in the ventilation measure contemporaneous with a further change in the leak measure.

21. The apparatus of claim 20 wherein the controller is further configured to determine a duration of the continuous mouth leak event, the duration beginning with the contemporaneous change and ending with the further contemporaneous change.

22. The apparatus of claim 21 wherein the contemporaneous change comprises an increase in the measure of leak and a decrease in the measure of ventilation, and the further contemporaneous change comprises a decrease in the measure of leak and an increase in the measure of ventilation.

23. The apparatus of claim 17 wherein the measure of ventilation comprises a low pass filtered absolute value of the measured flow divided in half, and wherein the measure of leak comprises an instantaneous leak determined as a function of a calculated leak conductance.

24. The apparatus of claim 17 wherein the analysis further determines a gradient with data representative of the leak measure.

25. The apparatus of claim 24 wherein the analysis integrates a product of the sign of the gradient and the covariance.

26. The apparatus of claim 25, wherein the identifying the continuous mouth leak event comprises scoring a continuous mouth leak based on a comparison of the integrated product with a threshold.

27. The apparatus of claim 17 further comprising:
wherein the sensor is a flow sensor, wherein the controller is configured to determine the measured flow of breathable gas with the flow sensor; and
a flow generator configured to produce a breathable gas for a patient at a pressure above atmospheric pressure, wherein the controller is further configured to control the flow generator to produce the breathable gas according to a pressure therapy regime based on the identified continuous mouth leak.

28. The apparatus of claim 27 wherein the controller being coupled with the sensor and the flow generator and configured to control the flow generator to produce the breathable gas according to the pressure therapy regime, the controller includes: a leak detection module configured to detect a leak event based on an analysis of the measured flow; and a pressure adjustment module configured to adjust a therapeutic pressure supplied by the flow generator as a function of a magnitude of an output of the leak detection module, the adjustment for reducing the detected leak event.

29. The apparatus of claim 28 wherein the leak detection module is configured to detect the continuous mouth leak event.

30. The apparatus of claim 28 wherein the pressure adjustment module is configured to decrease pressure as a function of the leak event.

31. The apparatus of claim 28 wherein the pressure adjustment module is configured to increase pressure as a function of the leak event.

32. The apparatus of claim 28 wherein the pressure adjustment module is configured to analyze a patient flow signal to calculate an adjustment probability for an increase of pressure and a decrease of pressure.

33. The apparatus of claim 32 wherein the pressure adjustment module is configured to adjust pressure based on a comparison of the adjustment probability and a threshold.

34. The apparatus of claim 32, wherein the controller is further configured to access data representing a measured flow of breathable gas so as to: determine a plurality of features from the ventilation measure and the leak measure; analyze the plurality of features with a time threshold and a magnitude threshold; and based on the analysis, set a leak indicator representative of the continuous mouth leak event.

35. The apparatus of claim 34 wherein the plurality of features comprise a first feature and a second feature, and wherein the analysis comprises evaluation of the first feature to detect a change in the first feature existing for a pre-determined period of time attributable to the time threshold; and wherein the analysis further comprises a comparison of the second feature with the magnitude threshold, based on the comparison of the first feature detecting the change for the pre-determined period of time.

36. The apparatus of claim 35 wherein the first feature comprises a modified covariance signal and the second feature comprises a covariance sum.

37. The leak detection apparatus of claim 17 wherein the controller is configured to: determine a plurality of features from the determined ventilation measure and leak measure; analyze the plurality of features with a time threshold and a magnitude threshold; based on the analysis, set a leak indicator, the leak indicator representative of the continuous mouth leak event.

38. The apparatus of claim 37 wherein the plurality of features comprise first and second features, and wherein the analysis comprises evaluation of the first feature to detect a change in the first feature existing for a pre-determined period of time attributable to the time threshold; and wherein the analysis further comprises a comparison of the second feature with the magnitude threshold based on the comparison of the first feature detecting the change for the pre-determined period of time.

39. The apparatus of claim 38 wherein the first feature comprises a modified covariance signal.

40. The apparatus of claim 39 wherein the change in the first feature is negative.

41. The apparatus of claim 39 wherein the second feature comprises a covariance sum.

42. The apparatus of claim 41 wherein the leak indicator is set to represent the continuous mouth leak event if the comparison detects that the second feature falls below the magnitude threshold.

43. The apparatus of claim 41 wherein the first and second features are derived from the ventilation measure and the leak measure.

44. The apparatus of claim 37 further comprising:
wherein the sensor is a flow sensor, wherein the controller is configured to determine the measured flow of breathable gas with the flow sensor; and
a flow generator configured to produce a breathable gas for a patient at a pressure above atmospheric pressure, wherein the controller is further configured to control the flow generator to produce the breathable gas according to a pressure therapy regime.

45. The apparatus of claim 44 wherein the controller is further configured to control the flow generator to produce the breathable gas according to the pressure therapy regime based on the leak indicator.

46. The apparatus of claim 17 wherein the controller is configured to determine the ventilation measure from samples of the measured flow over a period of time.

47. The apparatus of claim 17 wherein the controller is configured to determine the ventilation measure based on an absolute value of the measured flow.

48. The apparatus of claim 17 wherein the controller is configured with a leak module to detect the contemporaneous change, and wherein data representing the contemporaneous change is applied to a mouth leak classifier module of the controller that is configured to identify the continuous mouth leak event based on the contemporaneous change and a plurality of threshold values stored in a memory of the controller.

49. The leak detection apparatus of claim 17 wherein the controller is configured to determine whether or not to adjust a setting of a pressure of the flow of breathable gas based on the covariance signal indicating a negative covariance.

50. A processor-readable medium, having stored thereon processor-executable instructions which, when executed by a processor, cause the processor to detect leak from a flow of breathable gas within a respiratory pressure treatment apparatus, the processor-executable instructions comprising:
instructions to measure the flow using a sensor;
instructions to determine a ventilation measure and a leak measure from the measured flow;
instructions to analyze the ventilation measure and the leak measure to detect a contemporaneous change comprising a change in the ventilation measure contemporaneous with a change in the leak measure; and
instructions to identify a leak event based on the contemporaneous change.

51. The processor-readable medium of claim 50 wherein the processor-executable instructions comprise a leak module to detect the contemporaneous change, and instructions to apply data representing the contemporaneous change to a mouth leak classifier module that is configured to identify the leak type based on the contemporaneous change and a plurality of stored threshold values.

* * * * *

UNITED STATES PATENT AND TRADEMARK OFFICE
CERTIFICATE OF CORRECTION

PATENT NO. : 10,328,219 B2
APPLICATION NO. : 13/812253
DATED : June 25, 2019
INVENTOR(S) : Dushyant Rao, Jeffrey Peter Armitstead and Dinesh Ramanan Page 1 of 1

It is certified that error appears in the above-identified patent and that said Letters Patent is hereby corrected as shown below:

On the Title Page

Under item (73) the Assignee section, "RedMed Pty Ltd" should read --ResMed Pty Ltd--

Signed and Sealed this
Twentieth Day of August, 2019

Andrei Iancu
*Director of the United States Patent and Trademark Office*